United States Patent
Moran et al.

(10) Patent No.: US 7,914,519 B2
(45) Date of Patent: Mar. 29, 2011

(54) CATHETER DEVICE

(75) Inventors: Derek Moran, Goleta, CA (US); Russell J. Redmond, Goleta, CA (US); Claude Vidal, Santa Barbara, CA (US); David Zaks, Merom Hagalil (IL); Rosa C. Becker, Merom Hagalil (IL)

(73) Assignee: Elcam Medical Agricultural Cooperative Association, Ltd., Kibbutz Baram (IL)

( * ) Notice: Subject to any disclaimer, the term of this patent is extended or adjusted under 35 U.S.C. 154(b) by 1113 days.

(21) Appl. No.: 11/159,348

(22) Filed: Jun. 23, 2005

(65) Prior Publication Data
US 2007/0010796 A1    Jan. 11, 2007

(51) Int. Cl.
  *A61M 25/00* (2006.01)
  *A61M 25/098* (2006.01)
  *A61M 25/16* (2006.01)
(52) U.S. Cl. .................. 604/534; 604/533; 604/523
(58) Field of Classification Search .................. 604/523, 604/533, 167.04, 534–539, 905
See application file for complete search history.

(56) References Cited

U.S. PATENT DOCUMENTS

| | | | |
|---|---|---|---|
| 4,405,163 A * | 9/1983 | Voges et al. ................ 285/305 |
| 4,723,550 A | 2/1988 | Bales et al. |
| 4,730,616 A | 3/1988 | Frisbie et al. |
| 4,753,238 A | 6/1988 | Gaiser |
| 4,769,017 A | 9/1988 | Fath et al. |
| 4,838,269 A | 6/1989 | Robinson et al. |
| 4,857,062 A | 8/1989 | Russell |
| 4,874,378 A | 10/1989 | Hillstead |
| 4,886,507 A | 12/1989 | Patton et al. |
| 4,895,346 A | 1/1990 | Steigerwald |
| 4,929,235 A | 5/1990 | Merry et al. |
| 4,932,633 A | 6/1990 | Johnson et al. |
| 4,950,255 A | 8/1990 | Brown et al. |
| 4,960,412 A | 10/1990 | Fink |
| 5,062,836 A | 11/1991 | Wendell |
| 5,073,168 A | 12/1991 | Danforth |
| 5,092,857 A | 3/1992 | Fleischhacken |
| 5,105,853 A | 4/1992 | Lie |
| 5,108,380 A | 4/1992 | Herlitze et al. |
| 5,125,915 A | 6/1992 | Berry et al. |
| 5,154,701 A | 10/1992 | Cheer et al. |
| 5,167,636 A | 12/1992 | Clement |

(Continued)

FOREIGN PATENT DOCUMENTS
EP  1002553  5/2000
(Continued)

*Primary Examiner* — Nicholas D Lucchesi
*Assistant Examiner* — Rebecca E Eisenberg
(74) *Attorney, Agent, or Firm* — Stein McEwen, LLP

(57) ABSTRACT

There is provided a connector for coupling to a guiding catheter including a housing defining a conduit communicating with the interior of the guiding catheter, the housing including first and second housing portions which are manually positionable in various relative mutual axial orientations, a selectably openable normally closed valve associated with the conduit for selectable sealing thereof, the selectably openable valve having an open state, a closed state and at least one partially open state realized by suitable relative mutual axial orientation of the first and second housing portions and permitting at least one elongate element to extend therethrough, even when the valve is, in the closed state, the selectably openable valve including a spring which urges the valve towards the closed state and an automatically engageable and manually disengageable valve state governing mechanism operative for automatically retaining the valve in, a state other than the closed state against the urging of the spring.

13 Claims, 32 Drawing Sheets

U.S. PATENT DOCUMENTS

| | | |
|---|---|---|
| 5,185,004 A | 2/1993 | Lashinski |
| 5,188,607 A | 2/1993 | Wu |
| 5,195,980 A * | 3/1993 | Catlin ................. 604/167.04 |
| 5,203,774 A | 4/1993 | Gilson et al. |
| 5,269,764 A | 12/1993 | Vetter et al. |
| 5,269,771 A * | 12/1993 | Thomas et al. ............ 604/539 |
| 5,273,546 A | 12/1993 | McLaughlin et al. |
| 5,290,277 A | 3/1994 | Vercimak et al. |
| 5,324,271 A | 6/1994 | Abiuso et al. |
| 5,336,192 A | 8/1994 | Palestrant |
| 5,338,313 A | 8/1994 | Mollenauer et al. |
| 5,338,314 A | 8/1994 | Ryan |
| 5,352,215 A | 10/1994 | Thome et al. |
| 5,395,352 A | 3/1995 | Penny |
| 5,478,331 A | 12/1995 | Heflin et al. |
| 5,501,426 A | 3/1996 | Atkinson et al. |
| 5,507,732 A | 4/1996 | McClure et al. |
| 5,509,433 A | 4/1996 | Paradis |
| 5,514,109 A | 5/1996 | Mollenauer et al. |
| 5,531,723 A | 7/1996 | Solazzo |
| 5,562,618 A | 10/1996 | Cai et al. |
| 5,578,016 A | 11/1996 | Zinger |
| 5,591,137 A | 1/1997 | Stevens |
| 5,599,327 A | 2/1997 | Sugahara et al. |
| 5,632,729 A | 5/1997 | Cai et al. |
| 5,667,490 A | 9/1997 | Keith et al. |
| 5,685,866 A | 11/1997 | Lopez |
| 5,690,612 A | 11/1997 | Lopez et al. |
| 5,693,025 A | 12/1997 | Stevens |
| 5,694,686 A | 12/1997 | Lopez |
| 5,695,466 A | 12/1997 | Lopez |
| 5,699,821 A | 12/1997 | Paradis |
| RE35,841 E | 7/1998 | Frank et al. |
| 5,814,026 A | 9/1998 | Yoon |
| 5,873,862 A | 2/1999 | Lopez |
| 5,901,942 A | 5/1999 | Lopez |
| 5,911,710 A | 6/1999 | Barry et al. |
| 5,921,968 A | 7/1999 | Lampropoulos et al. |
| 5,928,204 A | 7/1999 | Lopez |
| 5,935,112 A | 8/1999 | Stevens et al. |
| 5,984,373 A | 11/1999 | Fitoussi et al. |
| 5,993,437 A | 11/1999 | Raoz |
| 6,024,729 A | 2/2000 | Dehdashtian et al. |
| 6,132,403 A | 10/2000 | Lopez |
| 6,142,981 A | 11/2000 | Heck et al. |
| 6,190,372 B1 | 2/2001 | Racz |
| 6,221,057 B1 | 4/2001 | Schwartz et al. |
| 6,228,060 B1 | 5/2001 | Howell |
| 6,254,589 B1 | 7/2001 | Raoz |
| 6,258,072 B1 | 7/2001 | Weinberger |
| 6,287,280 B1 | 9/2001 | Lampropoulos et al. |
| 6,331,176 B1 | 12/2001 | Becker et al. |
| 6,402,723 B1 | 6/2002 | Lampropoulos et al. |
| 6,458,103 B1 | 10/2002 | Albert et al. |
| 6,488,674 B2 | 12/2002 | Becker et al. |
| 6,511,434 B1 | 1/2003 | Haytman et al. |
| 6,562,023 B1 | 5/2003 | Marrs et al. |
| RE38,145 E | 6/2003 | Lynn |
| 6,572,590 B1 | 6/2003 | Stevens et al. |
| 6,572,592 B1 | 6/2003 | Lopez |
| 6,575,960 B2 | 6/2003 | Becker et al. |
| 6,599,273 B1 | 7/2003 | Lopez |
| 6,632,200 B2 | 10/2003 | Potter et al. |
| 6,651,956 B2 | 11/2003 | Miller |
| 6,663,599 B2 | 12/2003 | Osbourne et al. |
| 6,669,673 B2 | 12/2003 | Lopez |
| 6,682,509 B2 | 1/2004 | Lopez |
| 6,695,820 B1 | 2/2004 | Armstrong et al. |
| 6,755,806 B1 | 6/2004 | Von Casimir |
| 6,758,833 B2 | 7/2004 | Lopez |
| 6,776,774 B2 | 8/2004 | Tansey, Jr. et al. |
| 6,817,995 B1 | 11/2004 | Halpern |
| 2002/0111585 A1 | 8/2002 | Lafontaine |
| 2004/0002684 A1 | 1/2004 | Lopez |
| 2004/0073174 A1 | 4/2004 | Lopez |
| 2004/0243070 A1 | 12/2004 | Lopez |

FOREIGN PATENT DOCUMENTS

| | | |
|---|---|---|
| WO | WO 93/11828 | 6/1993 |
| WO | WO 94/14497 | 7/1994 |
| WO | WO 98/23313 | 6/1998 |
| WO | WO 00/41624 | 7/2000 |

* cited by examiner

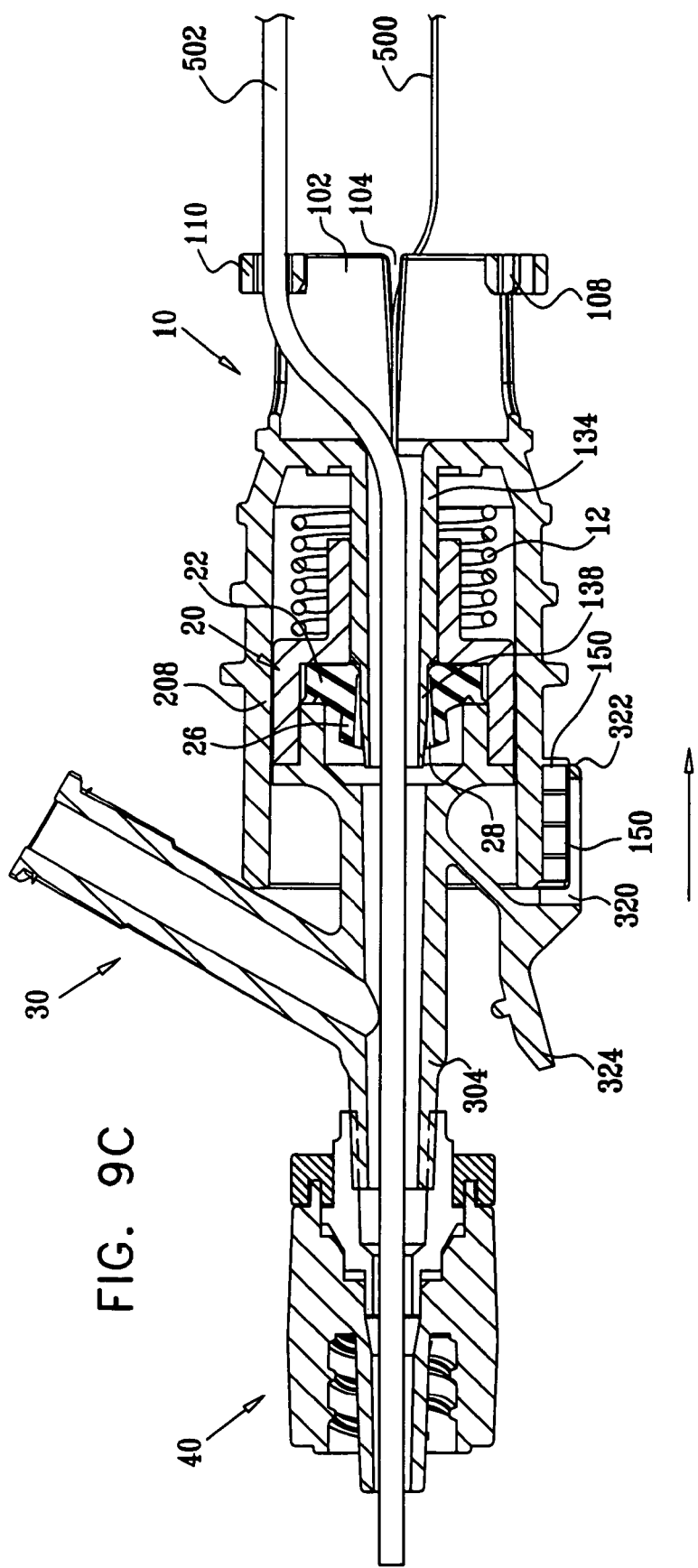

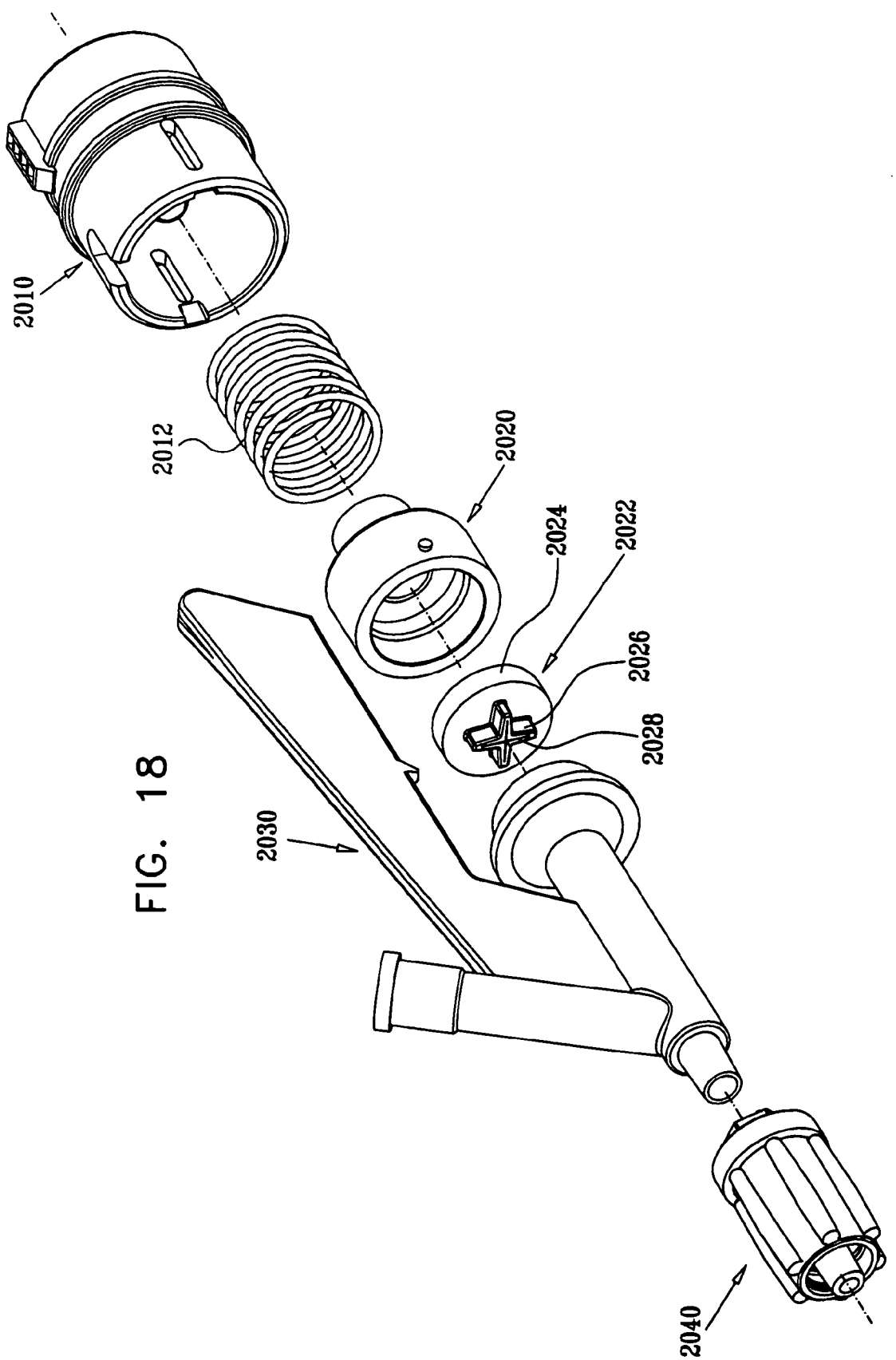

US 7,914,519 B2

CATHETER DEVICE

FIELD OF THE INVENTION

The present invention relates to catheter devices generally.

BACKGROUND OF THE INVENTION

The following U.S. patents are believed to represent the current state of the art: U.S. Pat. Nos. 6,817,995; 6,562,023; 6,488,674; 6,254,589; 6,190,372; 5,993,437; 5,667,490; 5,632,729; 5,562,618; 5,531,723; 5,290,277; 5,188,607; 4,950,255 and 4,769,017.

SUMMARY OF THE INVENTION

The present invention seeks to provide an improved catheter connection device.

There is thus provided in accordance with a preferred embodiment of the present invention a connector for coupling to a guiding catheter including a housing defining a conduit communicating with the interior of the guiding catheter, the housing including first and second housing portions which are manually positionable in various relative mutual axial orientations, a selectably openable normally closed valve associated with the conduit for selectable sealing thereof, the selectably openable valve having an open state, a closed state and at least one partially open state realized by suitable relative mutual axial orientation of the first and second housing portions and permitting at least one elongate element to extend therethrough, even when the valve is in the closed state, the selectably openable valve including a spring which urges the valve towards the closed state and an automatically engageable and manually disengageable valve state governing mechanism operative for automatically retaining the valve in a state other than the closed state against the urging of the spring.

In accordance with a preferred embodiment of the present invention the valve includes an elastomeric element having at least one slit therethrough. Additionally or alternatively, the connector includes at least one selectable retainer for selectably retaining the at least one elongate element against sliding motion relative to at least one of the first and second housing portions.

In accordance with another preferred embodiment of the present invention the automatically engageable and manually disengageable valve state governing mechanism is operative for fully closing the valve in a single stage operation of a user. Additionally or alternatively, the automatically engageable and manually disengageable valve state governing mechanism includes an engagement arm formed on the second housing element and having formed thereon a tooth and a serrated surface associated with the first housing element for engagement with the tooth.

There is also provided in accordance with another preferred embodiment of the present invention a connector for coupling to a guiding catheter including a housing defining a conduit communicating with the interior of the guiding catheter, the housing including first and second housing portions which are manually positionable in various relative mutual axial orientations, a selectably openable normally closed valve associated with the conduit for selectable sealing thereof, the selectably openable valve having an open state, a closed state and at least one partially open state realized by suitable relative mutual axial orientation of the first and second housing portions and permitting at least one elongate element to extend therethrough, even when the valve is in the closed state and a selectable retainer for selectably retaining the at least one elongate element against sliding motion relative to at least one of the first and second housing portions.

In accordance with a preferred embodiment of the present invention the selectable retainer is fixedly mounted onto the first housing portion. Alternatively, the selectable retainer is fixedly mounted onto the second housing portion. Preferably, the selectable retainer includes a manually operable locking mechanism for locking the at least one elongate element thereto.

In accordance with another preferred embodiment of the present invention the valve includes an elastomeric element having at least one slit therethrough. Preferably, the at least one selectable retainer includes at least one notch. Additionally or alternatively, the at least one selectable retainer includes at least one slot.

In accordance with a further preferred embodiment of the present invention the at least one selectable retainer includes at least one slot which is rotationally offset from the at least one notch. Preferably, the at least one elongate element includes at least first and second elongate elements, such that the first elongate element is retained in the at least one notch and is maintained separated from the second elongate element which is retained in the at least one slot.

BRIEF DESCRIPTION OF THE DRAWINGS

The present invention will be understood and appreciated more fully from the following detailed description, taken in conjunction with the drawings in which:.

FIGS. 9A, 9B and 9C are simplified sectional illustrations of the catheter connection device of FIGS. 8A and 8B in various operative orientations, which are taken along respective section lines IXA-IXA in FIG. 8A;

FIG. 18 is a simplified exploded view illustration of a catheter connection device constructed and operative in accordance with yet another preferred embodiment of the present invention;

DETAILED DESCRIPTION OF PREFERRED EMBODIMENTS

Figure 1:
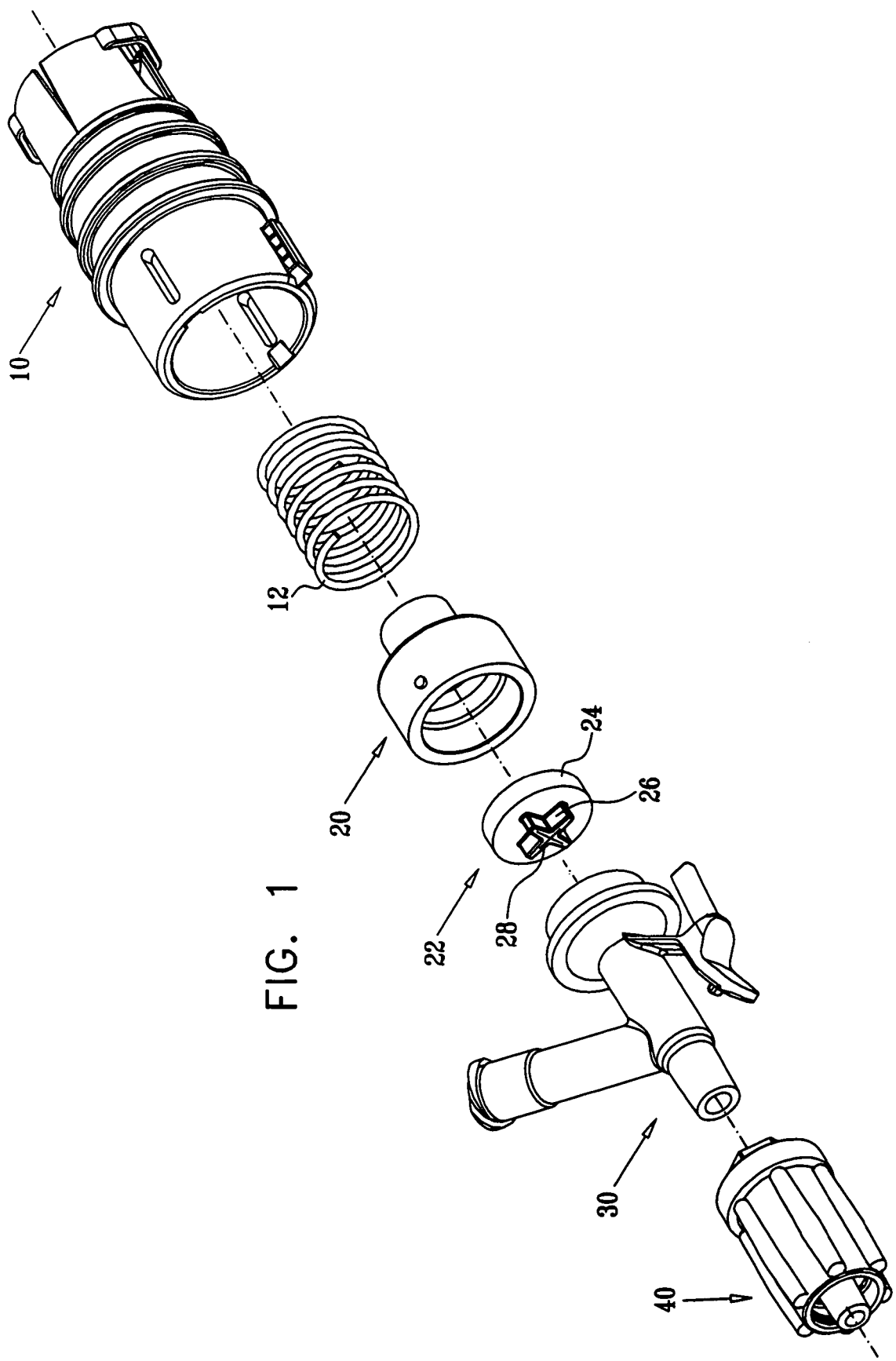
FIG. 1 is a simplified exploded view illustration of a catheter connection device constructed and operative in accordance with a preferred embodiment of the present invention.
Figure 2A:
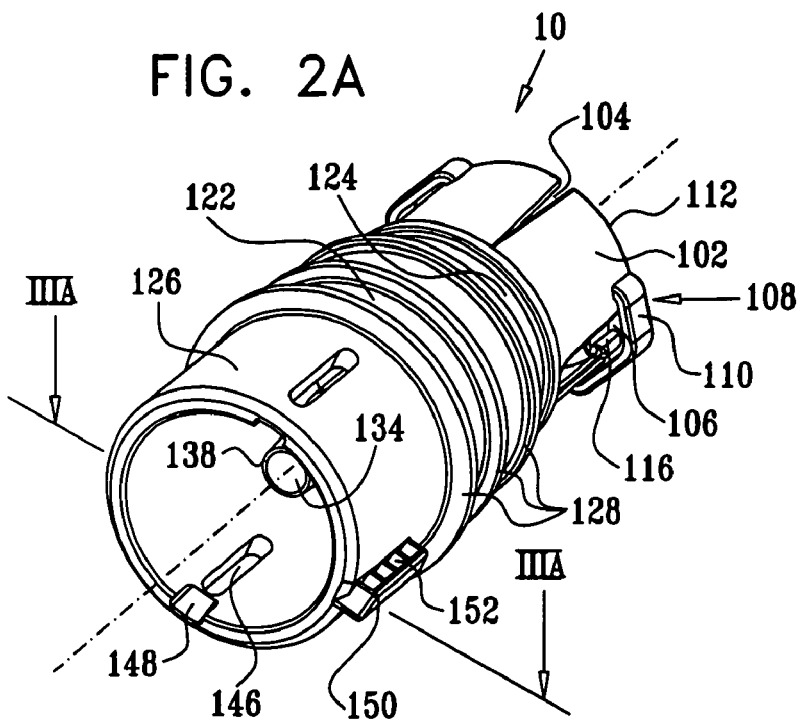
FIGS. 2A and 2B are simplified respective rearward facing and forward facing pictorial illustrations of a rear housing element which forms part of the catheter connection device of FIG. 1.
Figure 2B:
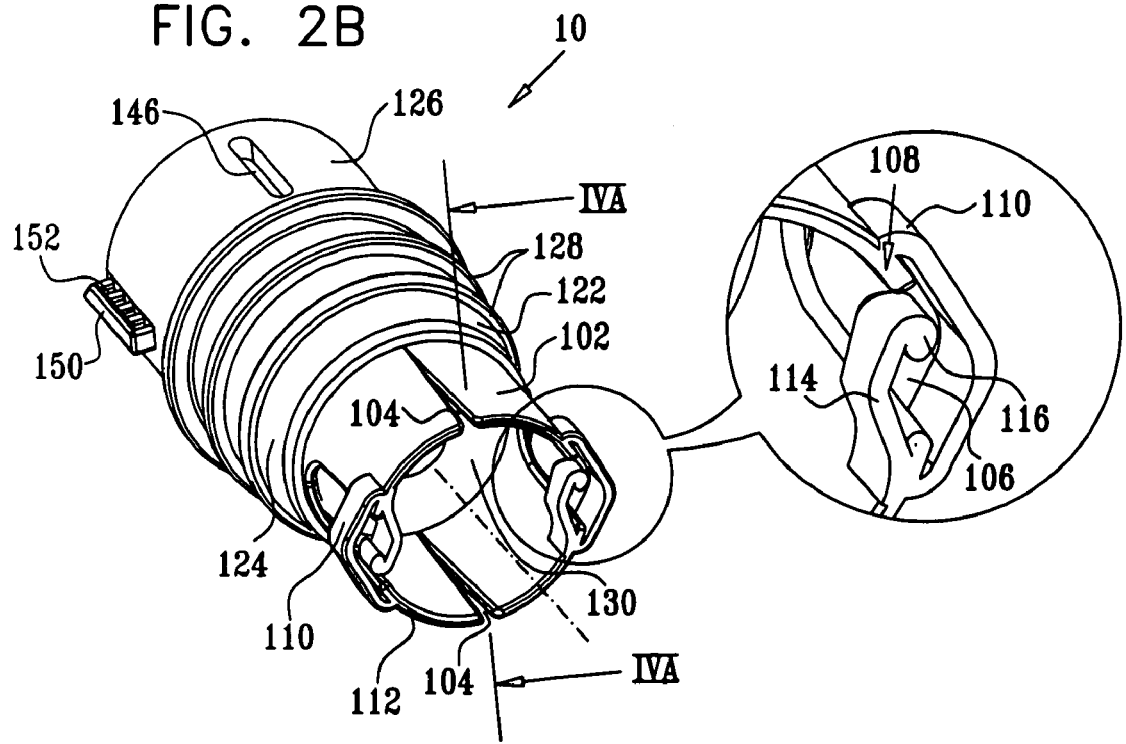
Figure 3A:
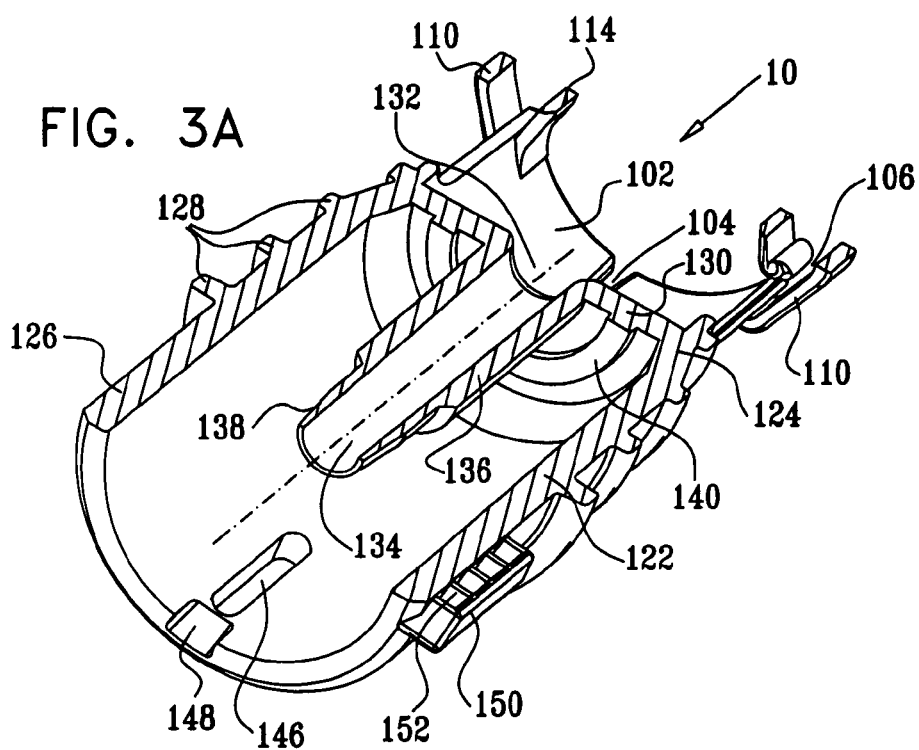
FIGS. 3A and 3B are, respectively, a simplified pictorial sectional illustration and a simplified sectional illustration taken along section lines IIIA-IIIA in FIG. 2A.
Figure 3B:
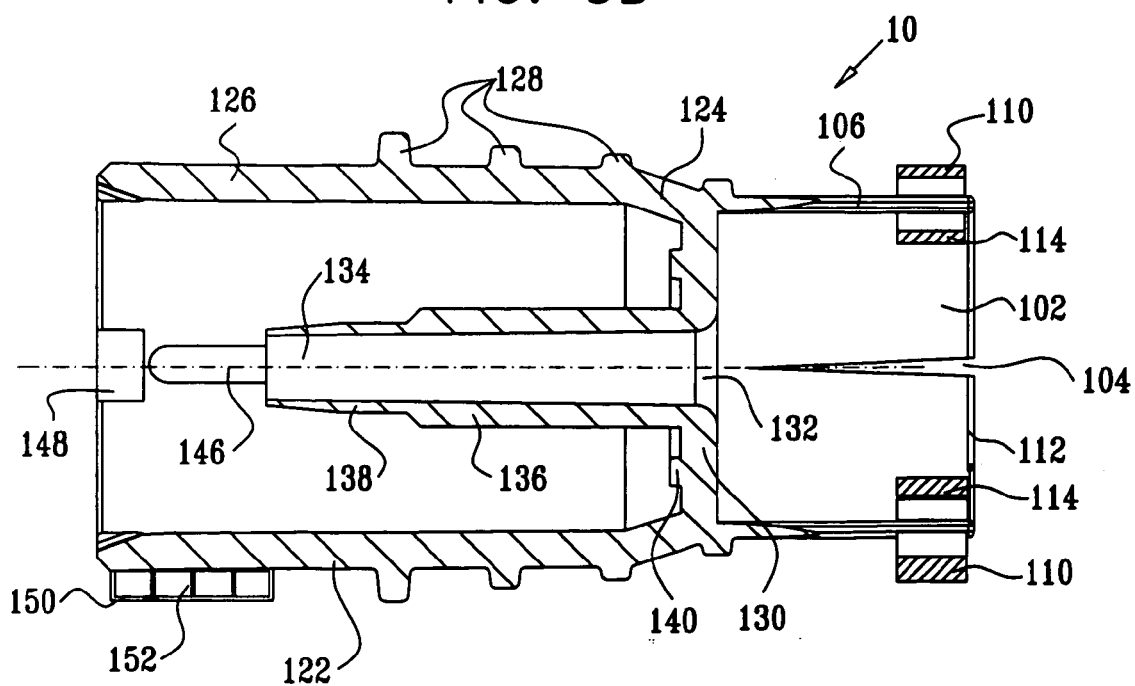
Figure 4A:
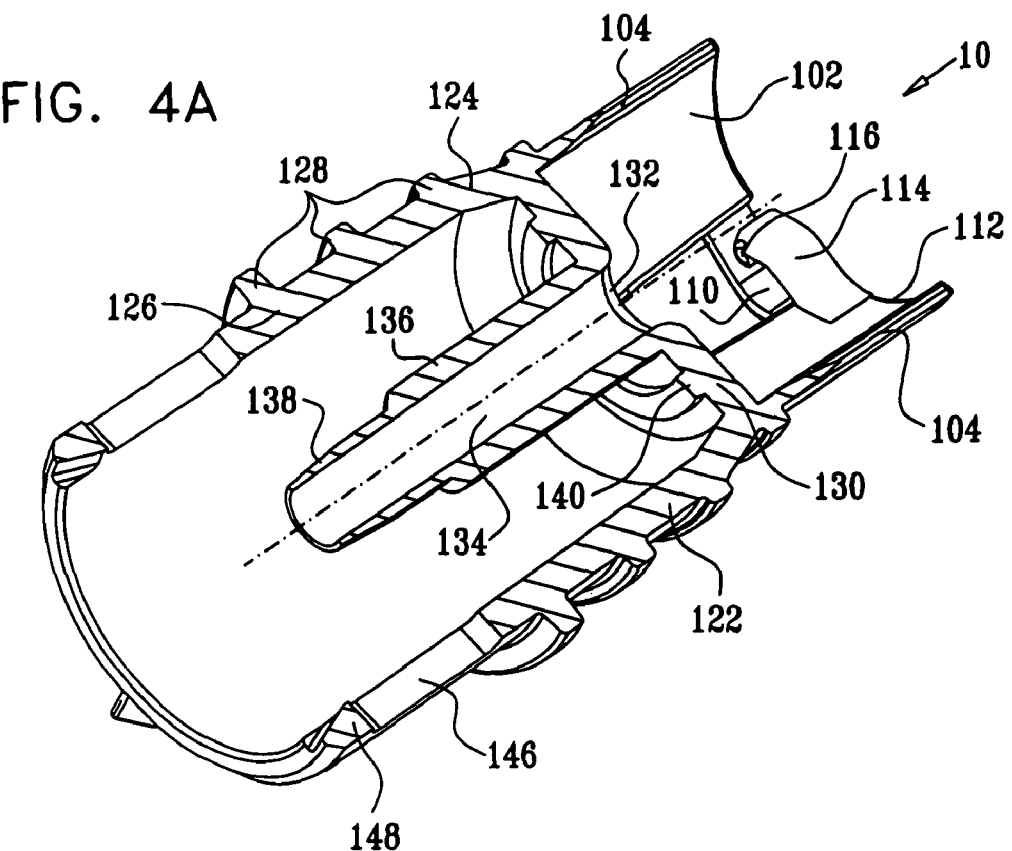
FIGS. 4A and 4B are, respectively, a simplified pictorial sectional illustration and a simplified sectional illustration taken along section lines IVA-IVA in FIG. 2B.
Figure 4B:
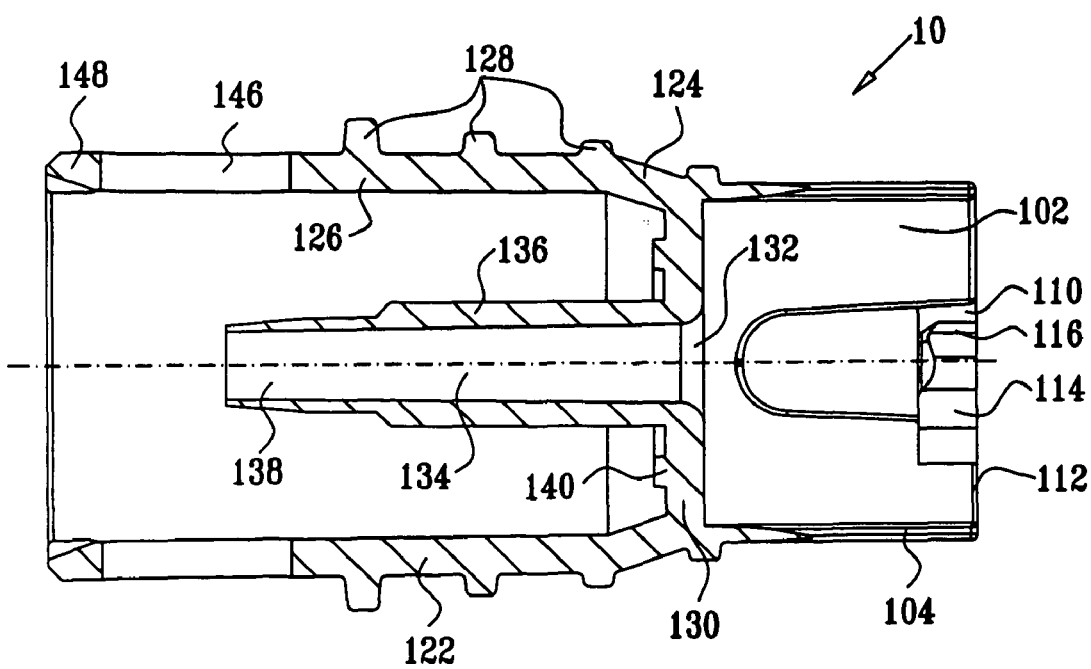
Figure 5A:
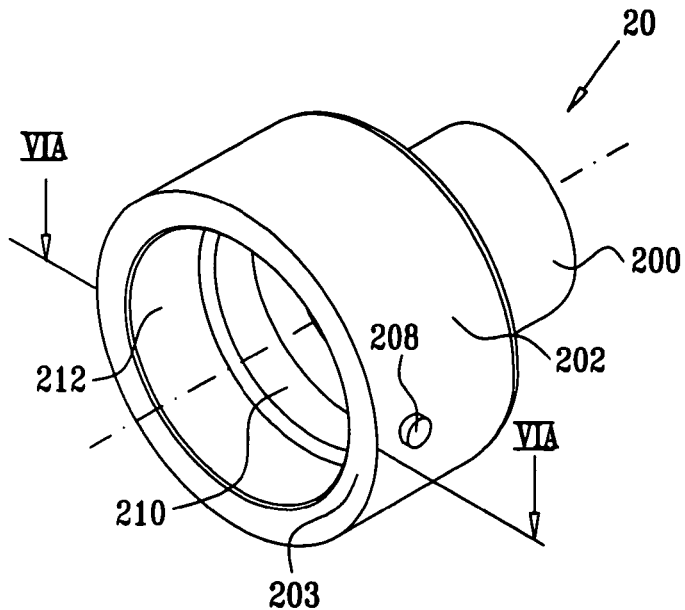
FIGS. 5A and 5B are simplified respective rearward facing and forward facing pictorial illustrations of an intermediate element which forms part of the catheter connection device of FIG. 1.
Figure 5B:
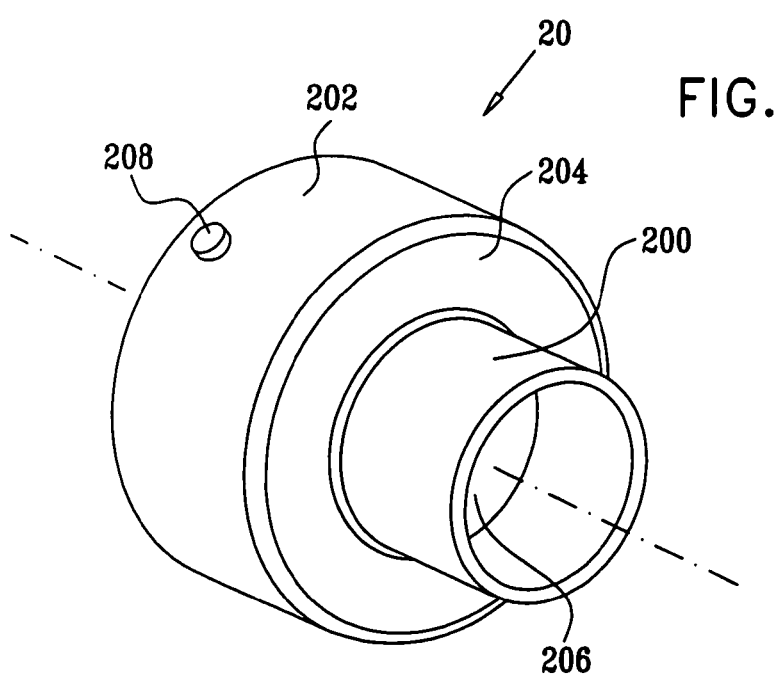
Figure 6A:
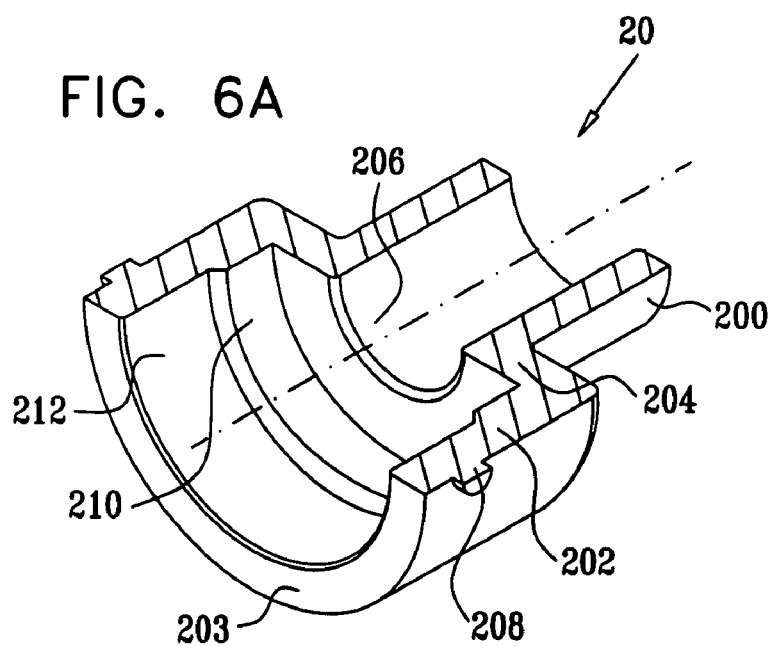
FIGS. 6A and 6B are, respectively, a simplified pictorial sectional illustration and a simplified sectional illustration taken along section lines VIA-VIA in FIG. 5A.
Figure 6B:
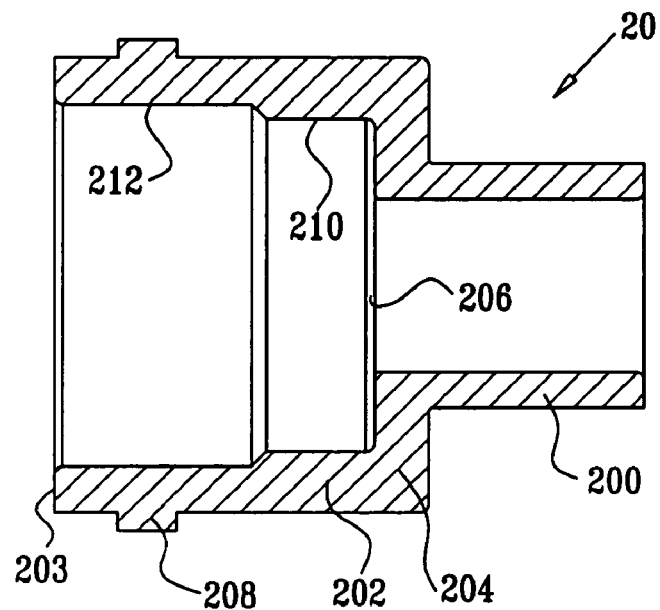

Reference is now made to FIGS. 1-9C, which illustrate a catheter connection device constructed and operative in accordance with a preferred embodiment of the present invention. Turning to FIG. 1, it is seen that the catheter connection device comprises a rear housing element 10, inside of which is located a spring 12, such as a coil spring, an intermediate element 20 and an elastomeric element 22, in the shape of a disc portion 24 and having a forward facing cross-shaped protrusion 26 integrally formed therewith and centered thereon. Cross-shaped protrusion 26 is formed with a throughgoing slit 28 and disk portion 24 is formed with a halfway going slit, positioned at a 90 degree angle with respect to slit 28. Mounted on intermediate element 20 is a branched connector 30, onto a forward end of which is mounted a tube connector assembly, such as catalog number 590205 which is commercially available from ELCAM MEDICAL AGRICULTURAL COOPERATIVE ASSOCIATION LTD of Kibbutz Baram, Israel.

Reference is now made to FIGS. 2A-4B, which illustrate the rear housing element 10. As seen in FIGS. 2A-4B, the rear housing element 10 comprises a generally cylindrical rearward facing portion 102 having formed therein a pair of notches 104 mutually separated by 180 degrees and a pair of elongate slots 106, mutually separated by 180 degrees and offset from the notches 104 by 90 degrees. Alternatively, any other suitable offset angle may be provided between notches 104 and slots 106.

Positioned at each of slots 106 is a clamp 108, which includes an outer bridge portion 110, which spans the slot 106 at an rearward facing edge 112 of rearward facing portion 102, and an arm portion 114, which partially spans the slot 106 at rearward facing edge 112 and has a free end 116.

Integrally formed with rearward facing portion 102 is a forward facing portion 122 which includes a tapered section 124 followed by a generally cylindrical section 126. A plurality of mutually spaced, generally parallel radially outward facing rings 128 are formed at or near outer surfaces of tapered section 124 and generally cylindrical section 126 for improving grip of the catheter connection device by the user. Alternatively, the rings 128 may be obviated. A bulkhead 130 is defined between rearward facing portion 102 and forward facing portion 122 and is formed with a central aperture 132 which communicates between the interior of the rearward facing portion 102 and a forward facing generally cylindrical conduit 134, which is centered within tapered section 124 and generally cylindrical section 126. Forward facing generally cylindrical conduit 134 includes a main portion 136 and a forward facing tapered portion 138. A forward-facing ring 140 is formed on bulkhead 130, symmetrically about forward facing generally cylindrical conduit 134 and defines a seat for spring 12 (FIG. 1).

Formed on forward facing generally cylindrical section 126 is a pair of elongate slots 146, which are typically mutually separated by 180 degrees and which may be circumferentially aligned with notches 104. Disposed forwardly of and aligned with elongate slots 146 there are preferably formed inwardly and forwardly facing tapered recesses 148.

Formed on a radially outward surface of forward facing generally cylindrical section 126 is a ridge 150 having a serrated surface 152 on one side wall thereof. Ridge 150 may be circumferentially separated from elongate slots 146 by 90 degrees.

Reference is now made to FIGS. 5A-6B, which illustrate the intermediate element 20. As seen in FIGS. 5A-6B, intermediate element 20 comprises a rearward facing, generally cylindrical portion 200, which is arranged to be disposed about forward facing generally cylindrical conduit 134 of the rear housing element 10 (FIGS. 2A-4B), and about which spring 12 (FIG. 1) is disposed.

Integrally formed with rearward facing portion 200 is a forward facing cylindrical portion 202, including a forward facing surface 203. A bulkhead 204 is defined between rearward facing portion 200 and forward facing cylindrical portion 202 and is formed with a central aperture 206 which communicates therebetween. Forward facing cylindrical portion 202 is formed with a pair of radially outwardly extending protrusions 208. The interior surface of forward facing cylindrical portion 202 includes a relatively narrower rear portion 210 in which elastomeric element 22 (FIG. 1) is seated, and communicating with a relatively wider forward portion 212.

Figure 7A:
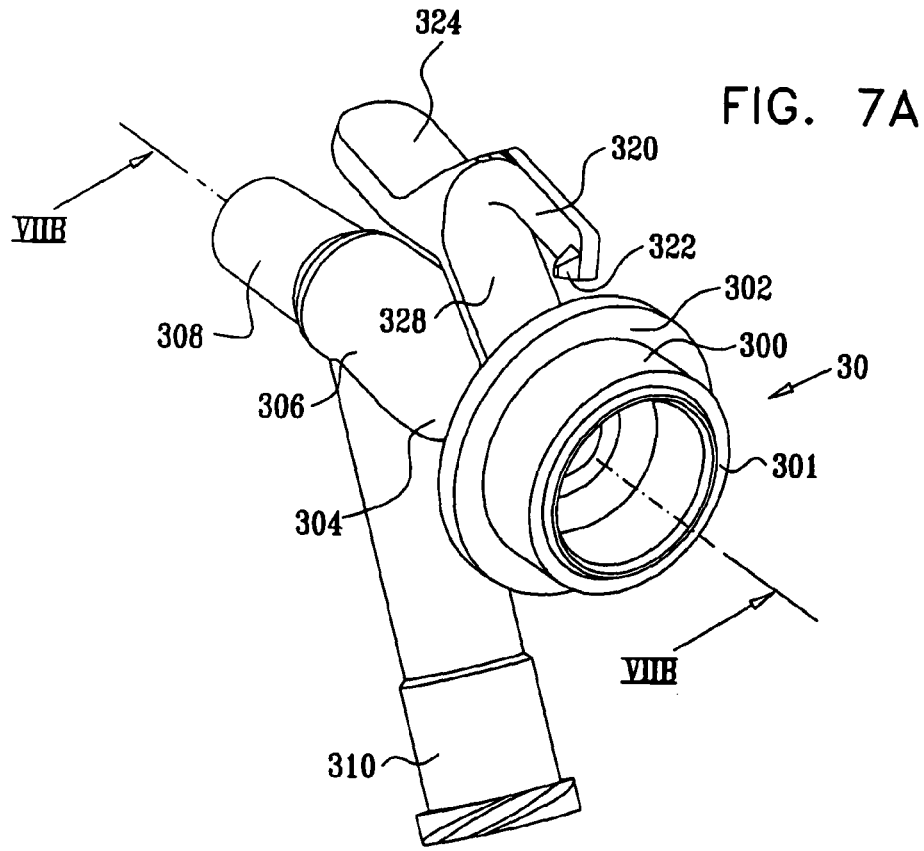
FIGS. 7A and 7B are, respectively, a simplified pictorial illustration and a simplified sectional illustration of a branched connector which forms part of the catheter connection device of FIG. 1, the sectional illustration being taken along section lines VIIB-VIIB in FIG. 7A.
Figure 7B:
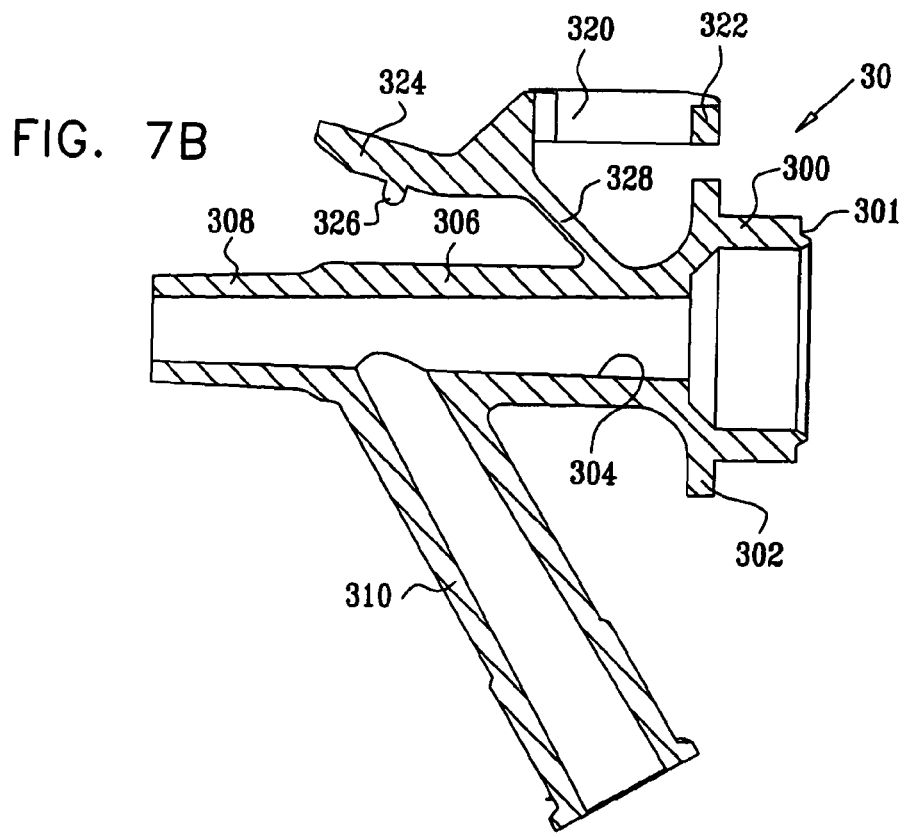

Reference is now made to FIGS. 7A & 7B, which illustrate the branched connector 30. As seen in FIGS. 7A & 7B, the branched connector 30 comprises a generally cylindrical rear portion 300 having a rearward facing surface 301 and a flange 302. Rear portion 300 is arranged to be seated within forward portion 212 of intermediate element 20 (FIGS. 5A-6B). Communicating with the interior of rear portion 300 is a generally cylindrical conduit 304, having a main portion 306 and a forward facing conical portion 308. Communicating with main portion 306, is a branch conduit 310.

Integrally formed with an outer surface of the branched connector 30 is a ratchet engagement arm 320 having a sideways facing outwardly extending tooth 322 for selectable engagement with serrated surface 152 of ridge 150 formed on rear housing element 10 (FIGS. 2A-3B). Ratchet engagement arm 320 is integrally formed with a finger engagement extension 324, which has a radially inwardly extending protrusion 326 formed on an underside thereof, to act as a stop and thus to limit radially outward positioning of tooth 322. Ratchet engagement arm 320 and finger engagement extension 324 are together mounted onto main portion 306 by an integrally formed flexible connection 328.

Figure 8A:
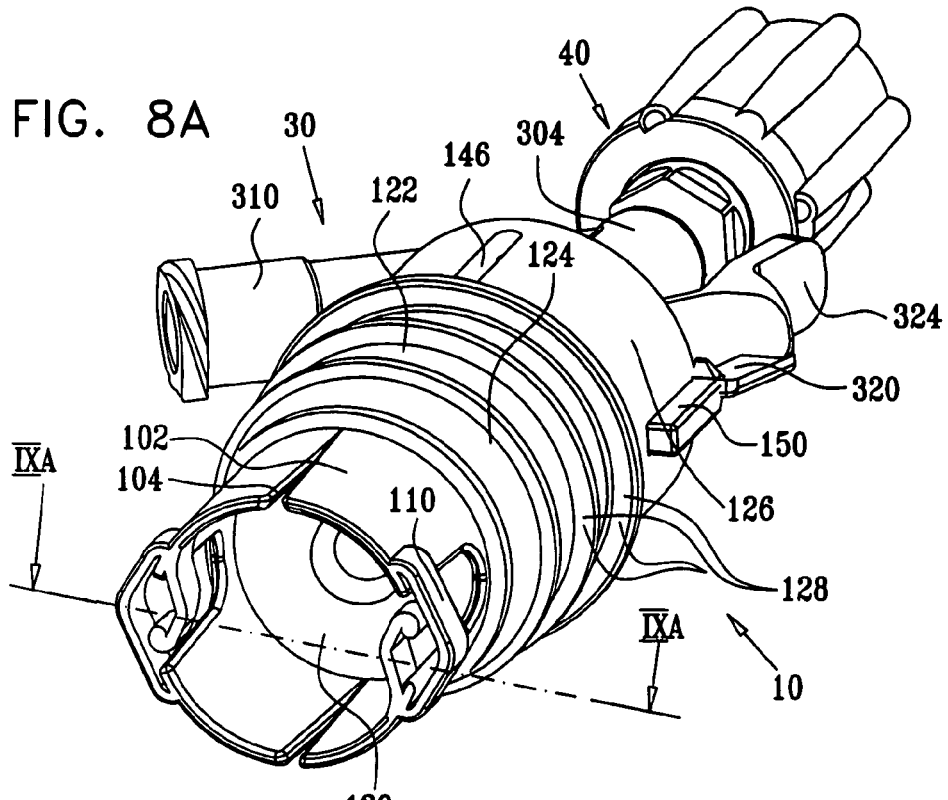
FIGS. 8A and 8B are rearward facing and forward facing pictorial view illustrations of the preferred embodiment of the catheter connection device of FIG. 1.
Figure 8B:
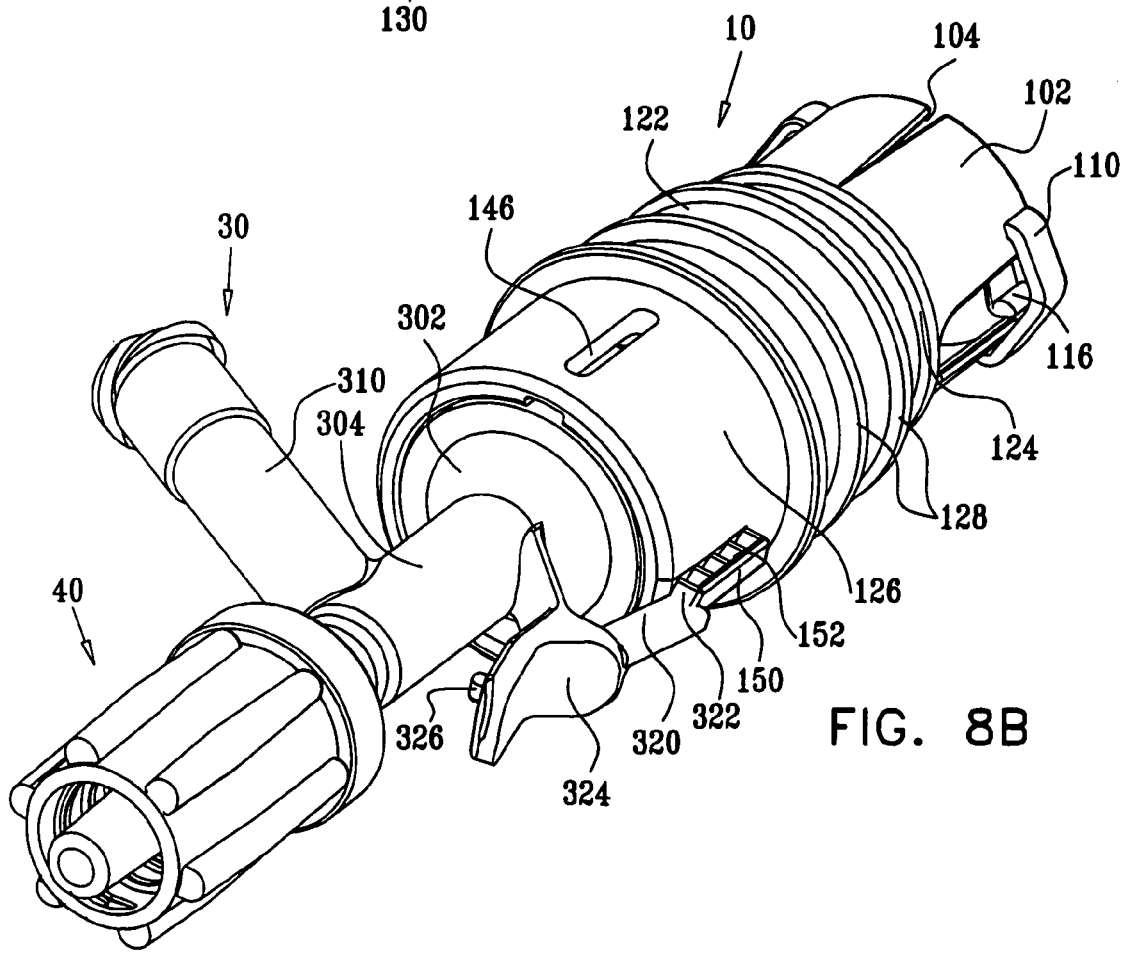
Figure 9A:
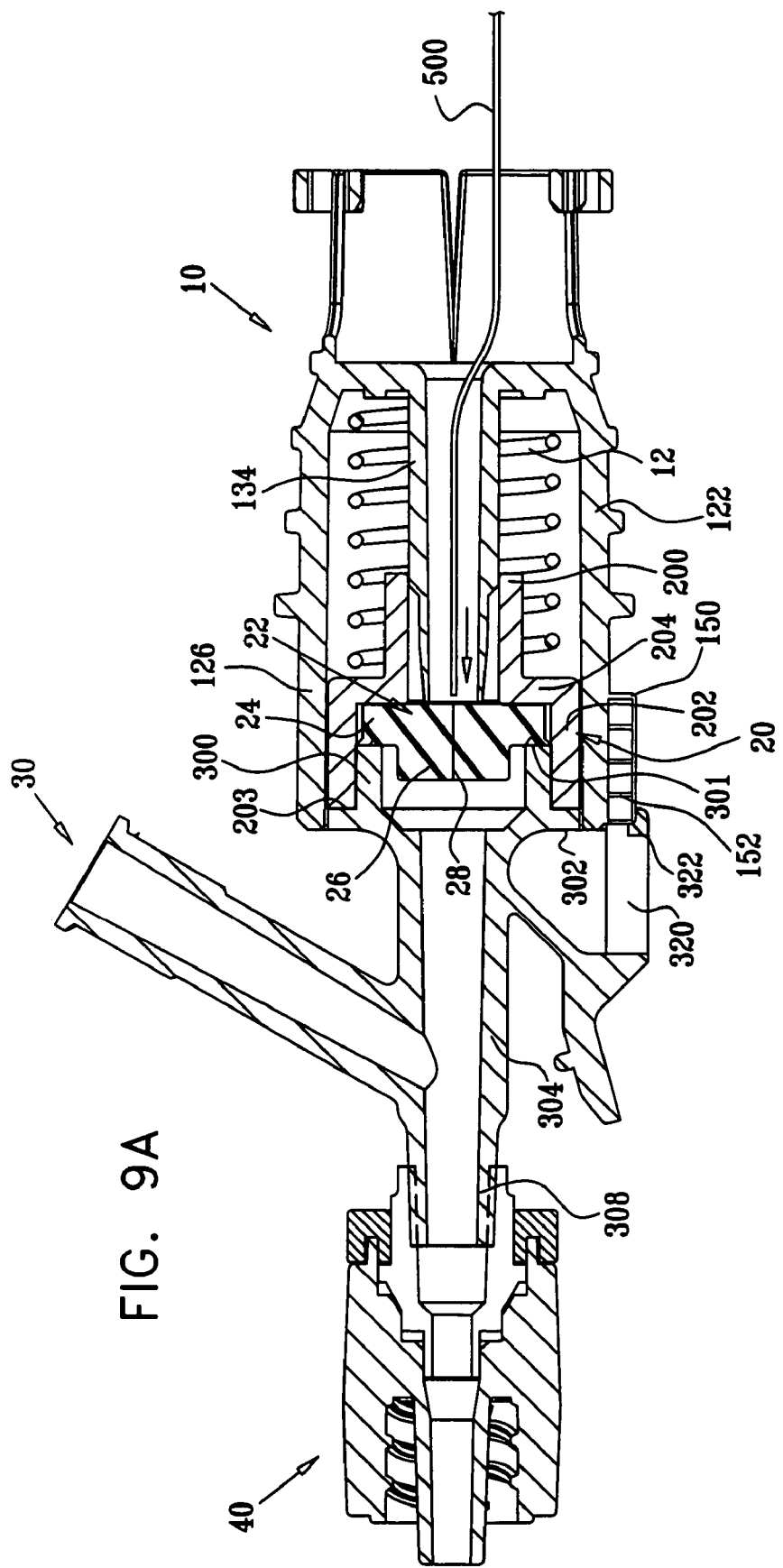
Figure 9B:
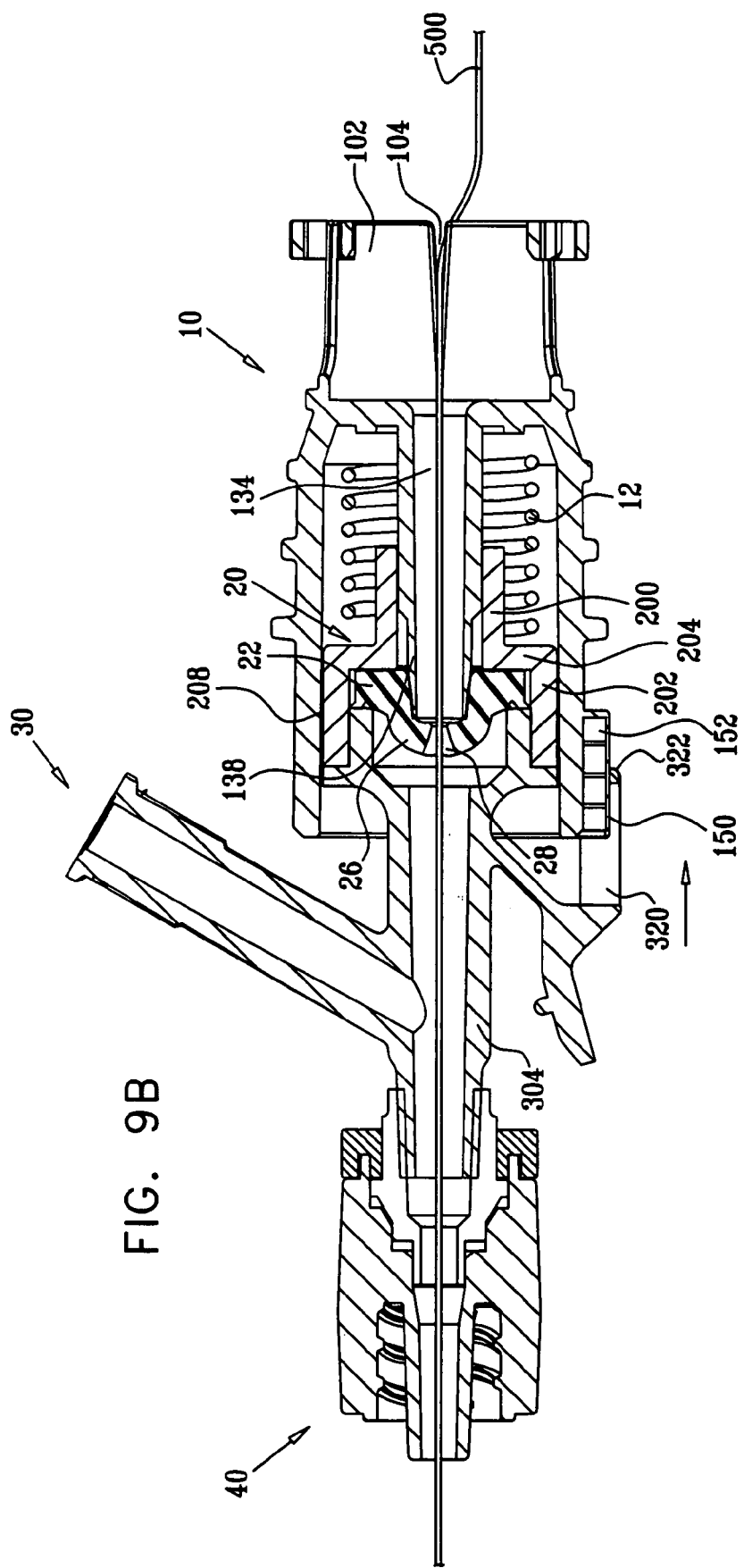

Reference is now made to FIGS. 8A and 8B, which are rearward facing and forward facing pictorial illustration of the catheter connection device of FIG. 1 and to FIGS. 9A, 9B and 9C which are simplified sectional illustrations of the catheter connection device of FIGS. 8A and 8B in various operative orientations, which are taken along respective section lines IXA-IXA in FIG. 8A.

Turning to FIG. 9A, the catheter connection device is shown in a closed operative orientation which is suitable for storage. In this orientation, cylindrical conduit 134 of rear housing element 10 is disposed within rearward facing portion 200 of intermediate element 20, and forward facing portion 202 of intermediate element 20 is disposed within cylindrical portion 126 of forward facing portion 122 of rear housing element 10. Protrusions 208 formed on forward facing cylindrical portion 202 (not shown) slidingly engage elongate slots 146 formed in cylindrical section 126 of rear housing element 10 (not shown). Spring 12 is preferably disposed about cylindrical conduit 134 of rear housing element 10 and rearward facing portion 200 of intermediate element 20.

Elastomeric element 22 is seated within forward portion 202 of intermediate element 20, against bulkhead 204. As seen clearly in FIG. 9A, in this operative orientation slit 28 is closed.

Rear portion 300 of branched connector 30 is seated in forward portion 202 of intermediate element 20, such that surface 203 thereof engages a rearward facing surface of flange 302 of branched connector 30, thus maintaining intermediate element 20 in place. Rearward facing surface 301 of rear portion 300 of branched connector 30 preferably engages disk portion 24 of elastomeric element 22, thus maintaining the elastomeric element in place.

Conical portion 308 of conduit 304 of branched connector 30 is disposed within a cylindrical portion of tube connector assembly 40.

Turning now to FIG. 9B, the catheter connection device is shown in a partially open operative orientation which is suitable for insertion of a narrow tube or guide wire 500 therethrough. In this orientation, branched connector 30 is rearwardly displaced, such that tooth 322 formed on ratchet arm 320 slides along serrated surface 152 of ridge 150 of rear housing element 10, stopping at a generally central part thereof.

Forward displacement of rear housing element 10 relative to branched connector 30 causes relative rearward displacement of intermediate element 20 within rear housing element 10, which is accompanied by relative rearward displacement of protrusions 208 within elongate slots 146 (Not shown). The relative rearward displacement of intermediate element 20 causes spring 12 to be partially-axially compressed.

Elastomeric element 22, which is seated between branched connector 30 and intermediate element 20, is relatively rearwardly displaced together with branched connector 30. Relative rearward displacement of elastomeric element 22 causes forward facing tapering portion 138 of cylindrical conduit 134 to partially extend through slit 28, thus creating a narrow passage between the rear end of the catheter connector device and the forward end thereof.

As seen in FIG. 9B, the narrow tube 500 may be inserted from the rear end of the catheter connector device to the forward end thereof via cylindrical conduit 134, slit 28, cylindrical conduit 304, and tube connector assembly 40. As shown clearly in FIG. 9B, once the narrow tube 500 is inserted through the catheter connector device, it may be engaged and retained in one of notches 104 formed in rearward facing portion 102, thus preventing axial movement of the tube 500 relative to rear housing element 10 and branched connector 30. Additionally, since the slit 28 is not fully opened, blood leakage is at least partially prevented.

Turning now to FIG. 9C, the catheter connection device is shown in an open operative orientation which is suitable for insertion of a tube 502 or a balloon catheter thereinto. In this orientation, branched connector 30 is further rearwardly displaced, such that tooth 322 formed on ratchet arm 320 slides along serrated surface 152 of ridge 150 of rear housing element 10, engaging the rearward portion thereof.

Relative rearward displacement of branched connector 30 causes rearward displacement of intermediate element 20 within rear housing element 10, which is accompanied with rearward displacement of protrusions 208 within elongate slots 146. The rearward displacement is limited by the engagement of protrusions 208 with the rearward facing surfaces of slots 146 (not shown). The rearward displacement of intermediate element 20 causes spring 12 to compress.

Elastomeric element 22, which is seated between branched connector 30 and intermediate element 20, is rearwardly displaced together with branched connector 30. Rearward displacement of elastomeric element 22 causes forward facing tapering portion 138 of cylindrical conduit 134 to fully extend through slit 28 of protrusion 26, thus creating a wide passageway through the catheter connector device.

As seen in FIG. 9C, a plurality of tubes 500 and 502 may be inserted from the rear end of the catheter connector device to the forward end thereof via cylindrical conduit 134, slit 28, cylindrical conduit 304, and tube connector assembly 40. As shown clearly in FIG. 9C, once the tubes 500 and 502 are inserted through the catheter connector device, at least one tube may be engaged and retained in one of notches 104 formed in rearward facing portion 102, thus preventing axial movement of the tube relative to rear housing element 10 and branched connector 30. Alternatively or additionally, at least one tube may be clamped by clamps 108, such that axial movement is enabled. The 90-degree separation of notches 104 and clamps 108 retains the tubes inserted through the catheter connector device in separate locations such that they do not get tangled.

It is appreciated that the catheter connector device may be manually returned to the closed orientation of FIG. 9A by a user pressing finger engagement extension 324 of ratchet engagement arm 320, thus releasing tooth 322 from serrated surface 152 of ridge 150. When the engagement between branched connector 30 and rear housing element 10 is released, spring 12 is released and returns to its extended rest position, thus forwardly displacing intermediate element 20, elastomeric element 22 and branched connector 30. It is appreciated that pressing the finger engagement extension 324 of the ratchet engagement arm 320 fully releases tooth 322, such that the tooth cannot get caught again in a manner that the catheter connector device is in a partially closed orientation.

It is appreciated that at the end of the catheterization and following removal of tubing and/or wires, forward displacement of the branched connector 30 releases the elastomeric element 22 thus allowing the elastomeric element 22 to return to its closed position by virtue of its elastomeric properties.

Figure 10:
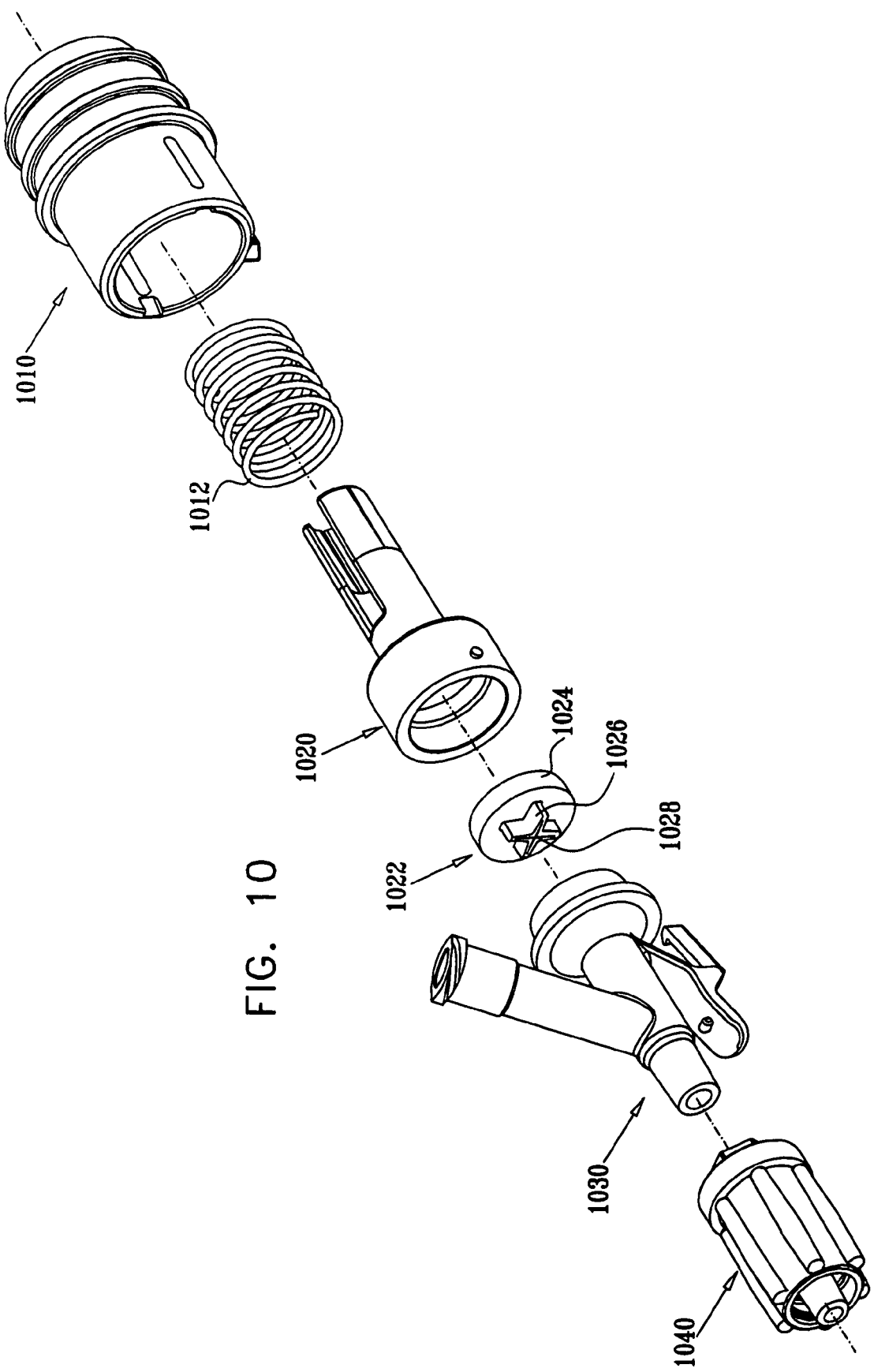
FIG. 10 is a simplified exploded view illustration of a catheter connection device constructed and operative in accordance with another preferred embodiment of the present invention.
Figure 11A:
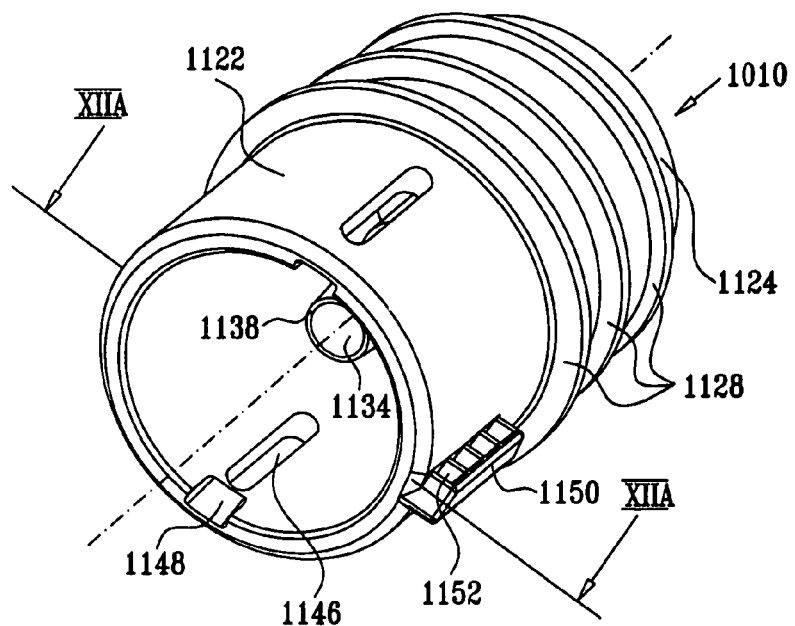
FIGS. 11A and 11B are simplified respective rearward facing and forward facing pictorial illustrations of a rear housing element which forms part of the catheter connection device of FIG. 10.
Figure 11B:
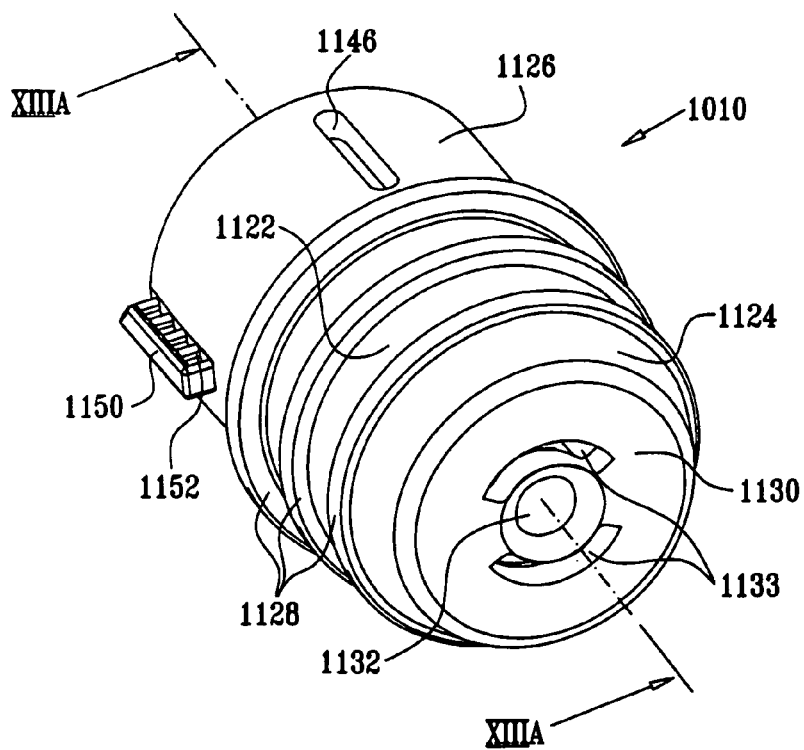
Figure 12A:
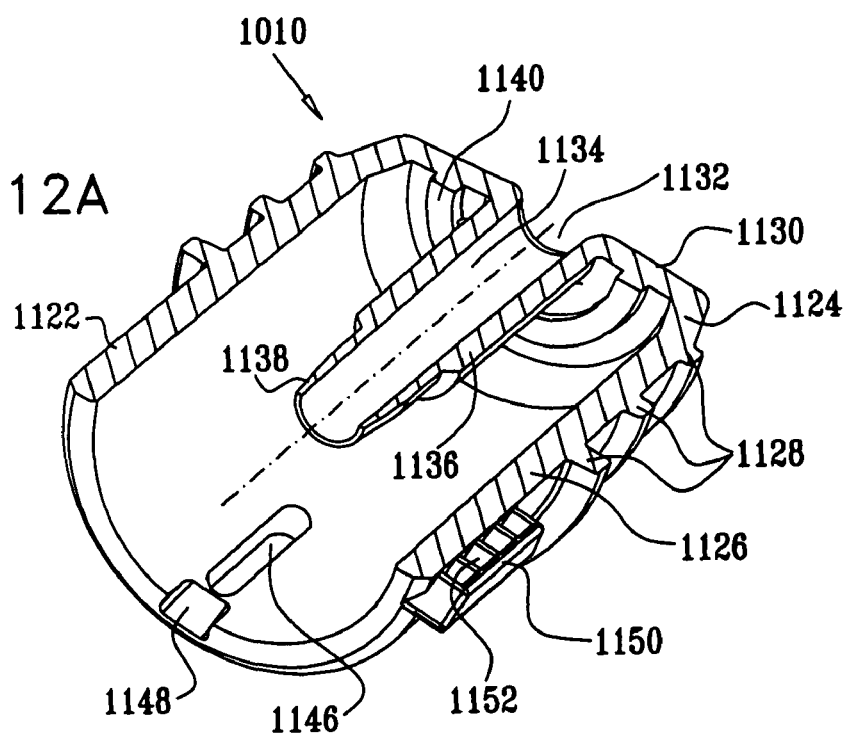
FIGS. 12A and 12B are, respectively, a simplified pictorial sectional illustration and a simplified sectional illustration taken along section lines XIIA-XIIA in FIG. 11A.
Figure 12B:
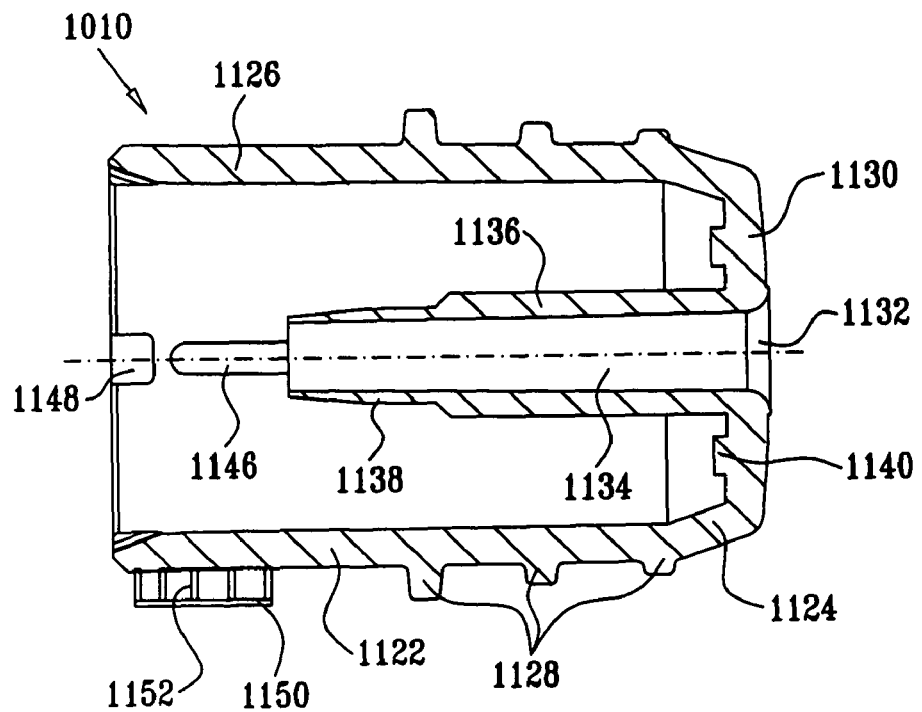
Figure 13A:
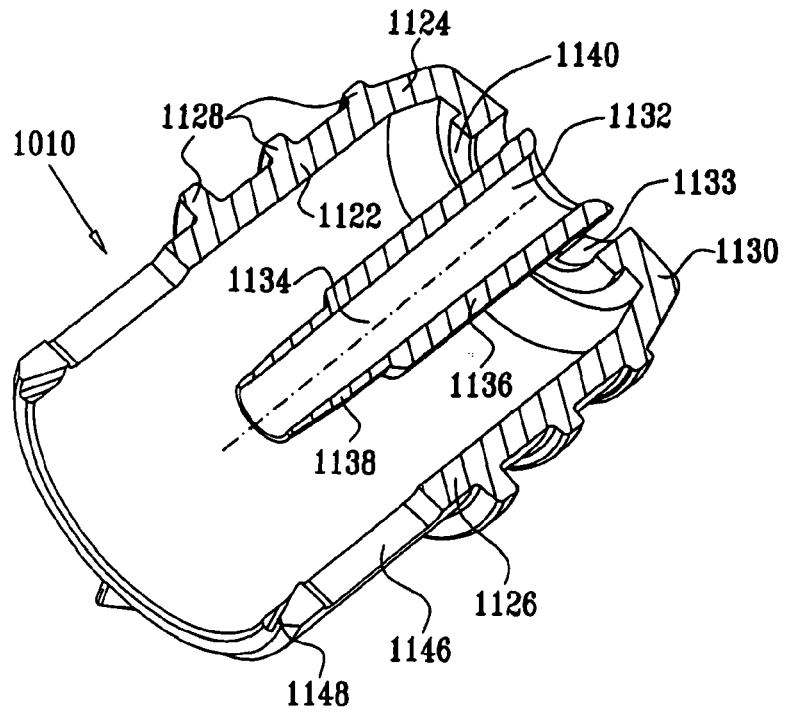
FIGS. 13A and 13B are, respectively, a simplified pictorial sectional illustration and a simplified sectional illustration taken along section lines XIIIA-XIIIA in FIG. 11B.
Figure 13B:
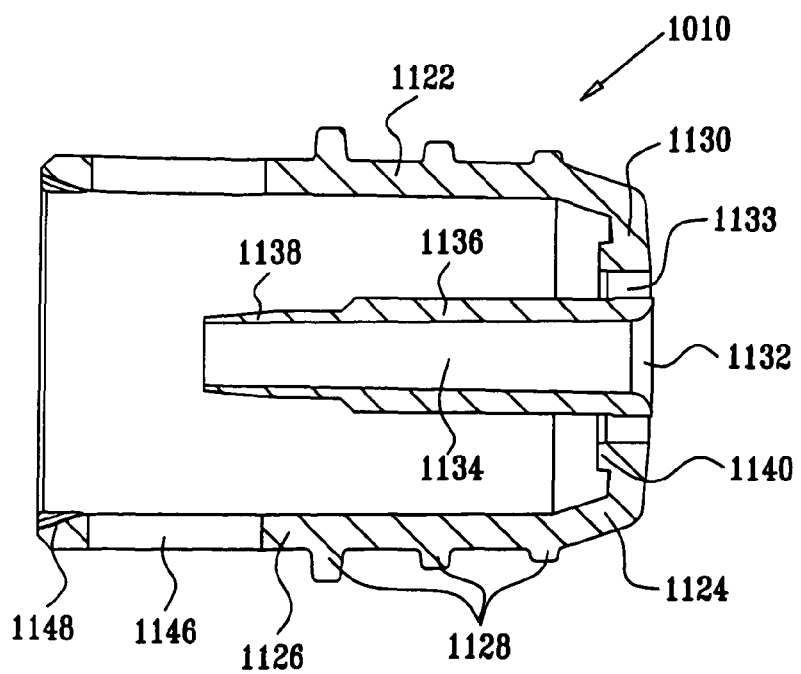
Figure 14A:
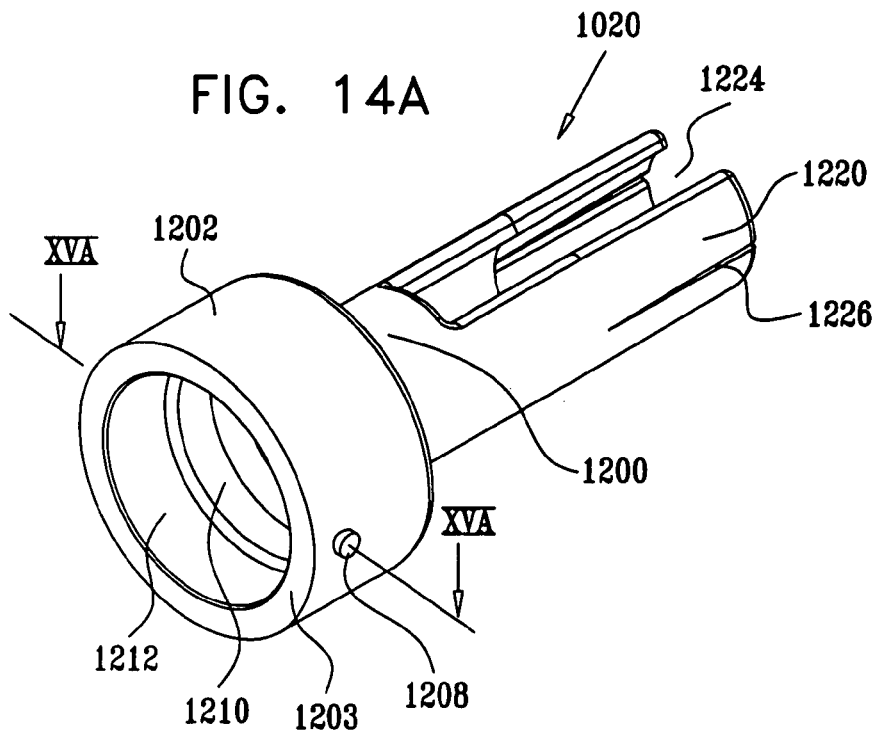
FIGS. 14A and 14B are simplified respective rearward facing and forward facing pictorial illustrations of an intermediate element which forms part of the catheter connection device of FIG. 10.
Figure 14B:
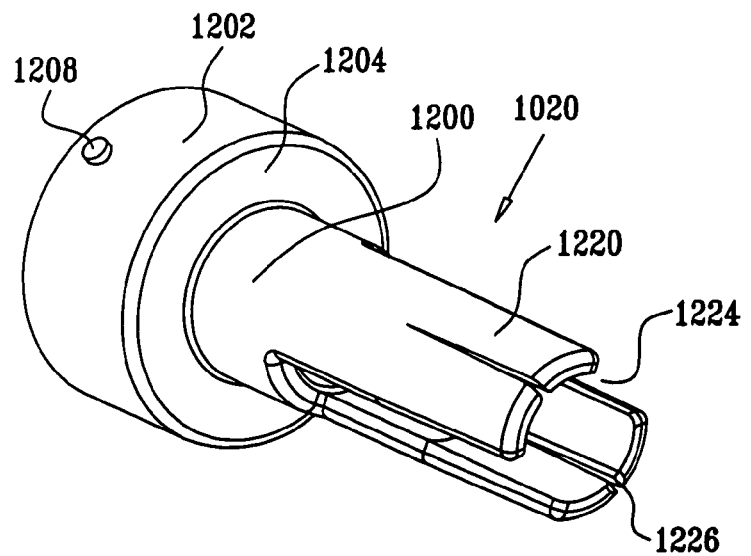
Figure 15A:
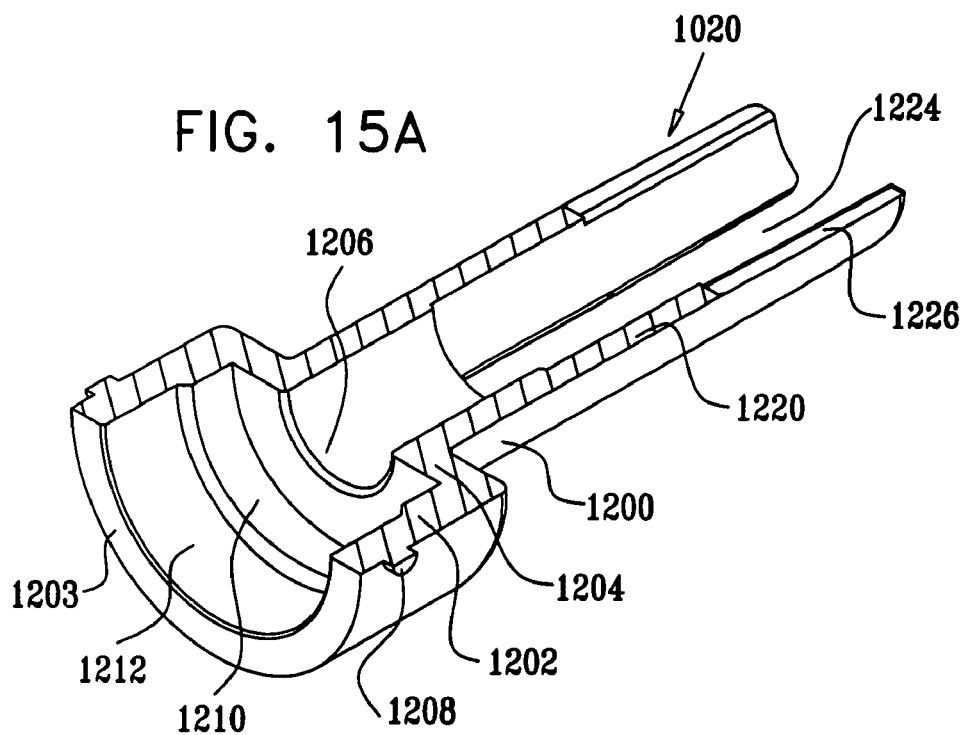
FIGS. 15A and 15B are, respectively, a simplified pictorial sectional illustration and a simplified sectional illustration taken along section lines XVA-XVA in FIG. 14A.
Figure 15B:
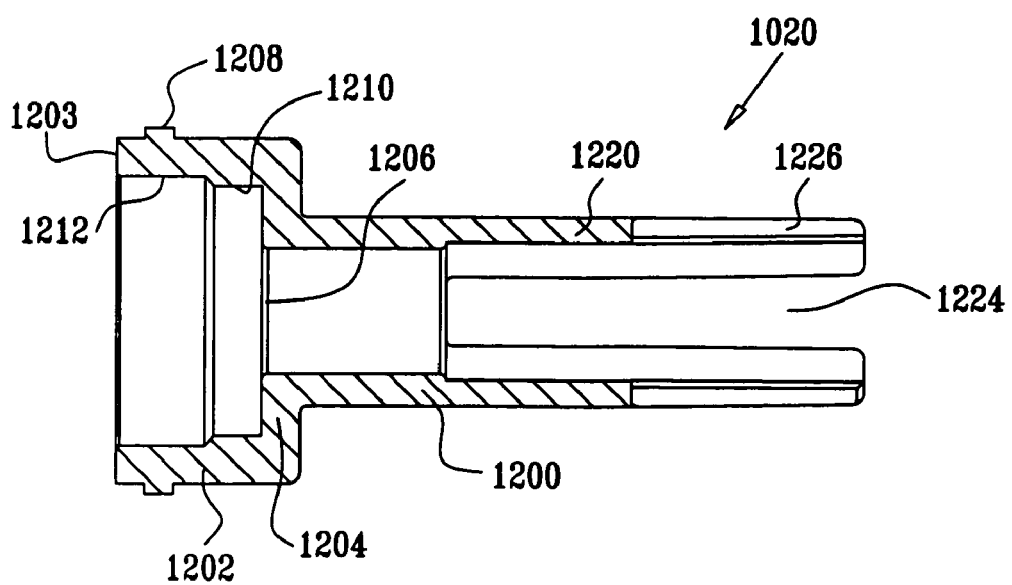

Reference is now made to FIGS. 10-17C, which illustrate a catheter connection device constructed and operative in accordance with another preferred embodiment of the present invention. Turning to FIG. 10, it is seen that the catheter connection device comprises a rear housing element 1010, inside of which is located a spring 1012, such as a coil spring, an intermediate element 1020 and an elastomeric element 1022, in the shape of a disc portion 1024 and a forward facing cross-shaped protrusion 1026 integrally formed therewith and centered thereon. Cross-shaped protrusion 1026 is formed with a throughgoing slit 1028 and disk portion 1024 is formed with a partial slit, positioned at a 90 degree angle with respect to slit 1028. Mounted on intermediate element 1020 is a branched connector 1030, onto a forward end of which is mounted a tube connector assembly 1040, such as catalog number 590205 which is commercially available from ELCAM MEDICAL AGRICULTURAL COOPERATIVE ASSOCIATION LTD of Kibbutz Baram, Israel.

Reference is now made to FIGS. 11A-13B, which illustrate the rear housing element 1010. As seen in FIGS. 12A-13B, the rear housing element 1010 comprises a main portion 1122 which includes a tapered section 1124 followed by a generally cylindrical section 1126. A plurality of mutually spaced, generally parallel radially outward facing rings 1128 are formed at or near outer surfaces of tapered section 1124 and generally cylindrical section 1126 for improving the grip of the catheter connector device by the user. It is appreciated that rings 1128 may be obviated.

Main portion 1122 terminates at a rearward end thereof in a wall portion 1130, which is formed with a central aperture 1132. Two generally concave slots 1133 are defined in wall portion 1130, surrounding aperture 1132. A forward facing generally cylindrical conduit 1134, which is centered within tapered section 1124 and generally cylindrical section 1126, extends forwardly of wall portion 1130 in fluid flow connection with central aperture 1132. Forward facing generally cylindrical conduit 1134 includes a main portion 1136 and a forward facing tapered portion 1138. A forward-facing ring 1140 is formed on wall portion 1130, symmetrically about forward facing generally cylindrical conduit 1134 and defines a seat for spring 1012 (FIG. 10).

Formed on forward facing generally cylindrical section 1126 is a pair of elongate slots. 1146, which are typically mutually separated by 180 degrees. Disposed forwardly of and aligned with elongate slots 1146 there are preferably formed inwardly and forwardly facing tapered recesses 1148.

Formed on a radially outward surface of forward facing generally cylindrical section 1126 is a ridge 1150 having a serrated surface 1152 on one side wall thereof. Ridge 1150 may be circumferentially separated from elongate slots 1146 by 90 degrees.

Reference is now made to FIGS. 14A-15B, which illustrate the intermediate element 1020. As seen in FIGS. 14A-15B, intermediate element 1020 comprises a rearward facing, generally cylindrical portion 1200. Integrally formed with rearward facing portion 1200 is a forward facing cylindrical portion 1202 including a forward facing surface 1203. A bulkhead 1204 is defined between rearward facing portion 1200 and forward facing cylindrical portion 1202 and is formed with a central aperture 1206 which communicates therebetween.

Forward facing cylindrical portion 1202 is formed with a pair of radially outwardly extending protrusions 1208. The interior surface of forward facing cylindrical portion 1202 includes a relatively narrower rear portion 1210 in which elastomeric element 1022 is seated, and communicating with a relatively wider forward portion 1212.

Extending rearwardly of rearward facing cylindrical portion 1200, are two generally concave wall portions 1220, separated by slots 1224. Wall portions 1220 have formed therein a pair of notches 1226 mutually separated by 180 degrees. The slots 1224 are offset from notches 1226 by 90 degrees.

Rearward facing ends of concave wall portions 1220 are adapted to be seated in slots 1133 about main portion 1136 of forward facing generally cylindrical conduit 1134 of the rear housing element 1010, and forward facing ends of concave wall portions 1220 and rearward facing cylindrical portion 1200 are arranged to be disposed about forward facing tapered portion 1138 of forward facing generally cylindrical conduit 1134 of the rear housing element 1010 (FIGS. 11A-13B). Spring 1012 (FIG. 10) is disposed about an outer surface of concave wall portions 1220 and rearward facing cylindrical portion 1200.

Figure 16A:
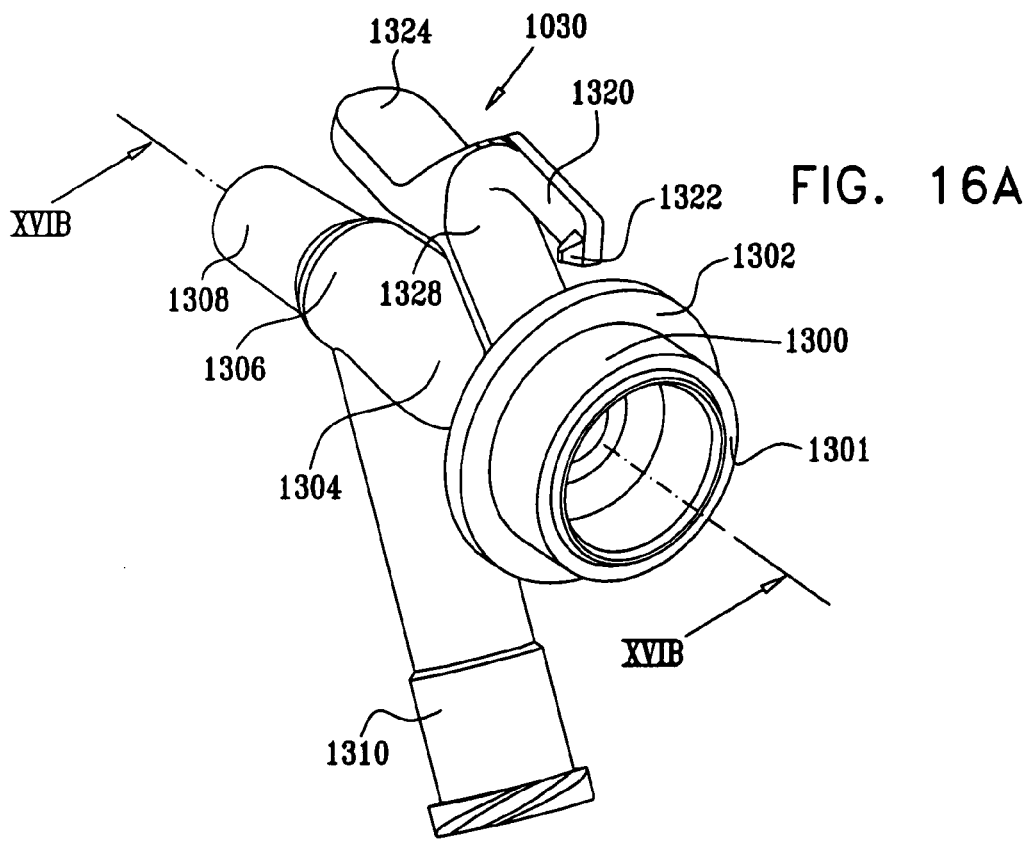
FIGS. 16A and 16B are, respectively, a simplified pictorial illustration and a simplified sectional illustration of a branched connector which forms part of the catheter connection device of FIG. 10, the sectional illustration being taken along section lines XVIB-XVIB in FIG. 16A.
Figure 16B:
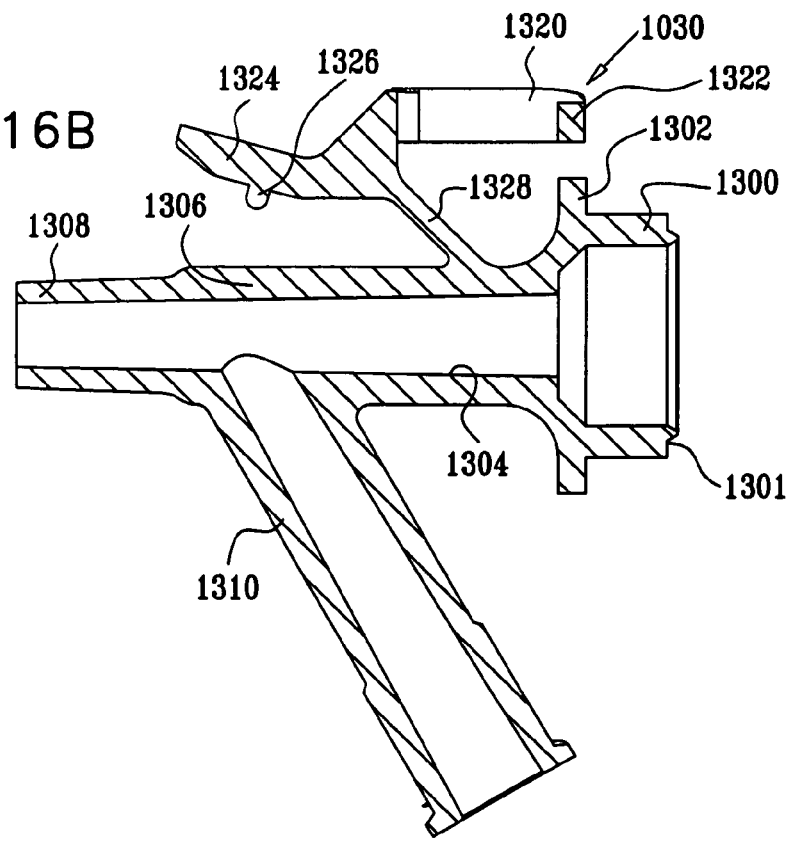

Reference is now made to FIGS. 16A & 16B, which illustrate the branched connector 1030. As seen in FIGS. 16A & 16B, the branched connector 1030 comprises a generally cylindrical rear portion 1300 having a rearward facing surface 1301 and a flange 1302. Rear portion 1300 is arranged to be seated within forward portion 1212 of intermediate element 1020 (FIGS. 14A-15B). Communicating with the interior of rear portion 1300 is a generally cylindrical conduit 1304, having a main portion 1306 and a forward facing conical conduit 1308. Communicating with main portion 1306 is a branch conduit 1310.

Integrally formed with an outer surface of the branched connector 1030 is a ratchet engagement arm 1320 having a sideways facing outwardly extending tooth 1322 for selectable engagement with serrated surface 1152 of ridge 1150 formed on rear housing element 1010 (FIGS. 11A-13B). Ratchet engagement arm 1320 is integrally formed with a finger engagement extension 1324, which has a radially inwardly extending protrusion 1326 formed on an underside thereof, to act as a stop and thus to limit radially outward positioning of tooth 1322. Ratchet engagement arm 1320 and finger engagement extension 1324 are together mounted onto main portion 1306 by an integrally formed flexible connection 1328.

Figure 17A:
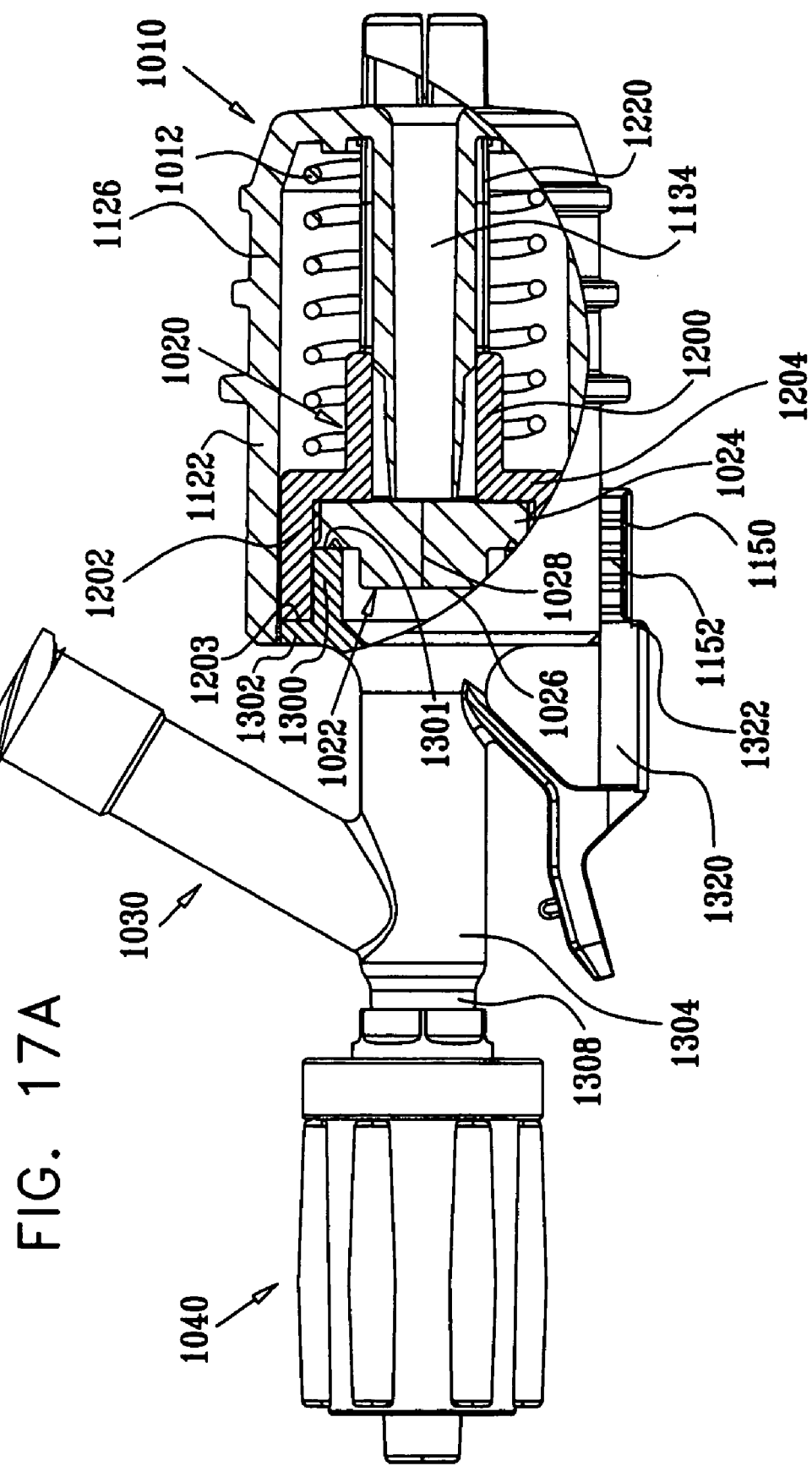
FIGS. 17A, 17B and 17C are partially cutout partially pictorial illustrations of the preferred embodiment of the catheter connection device of FIG. 10 in various operative orientations.
Figure 17B:
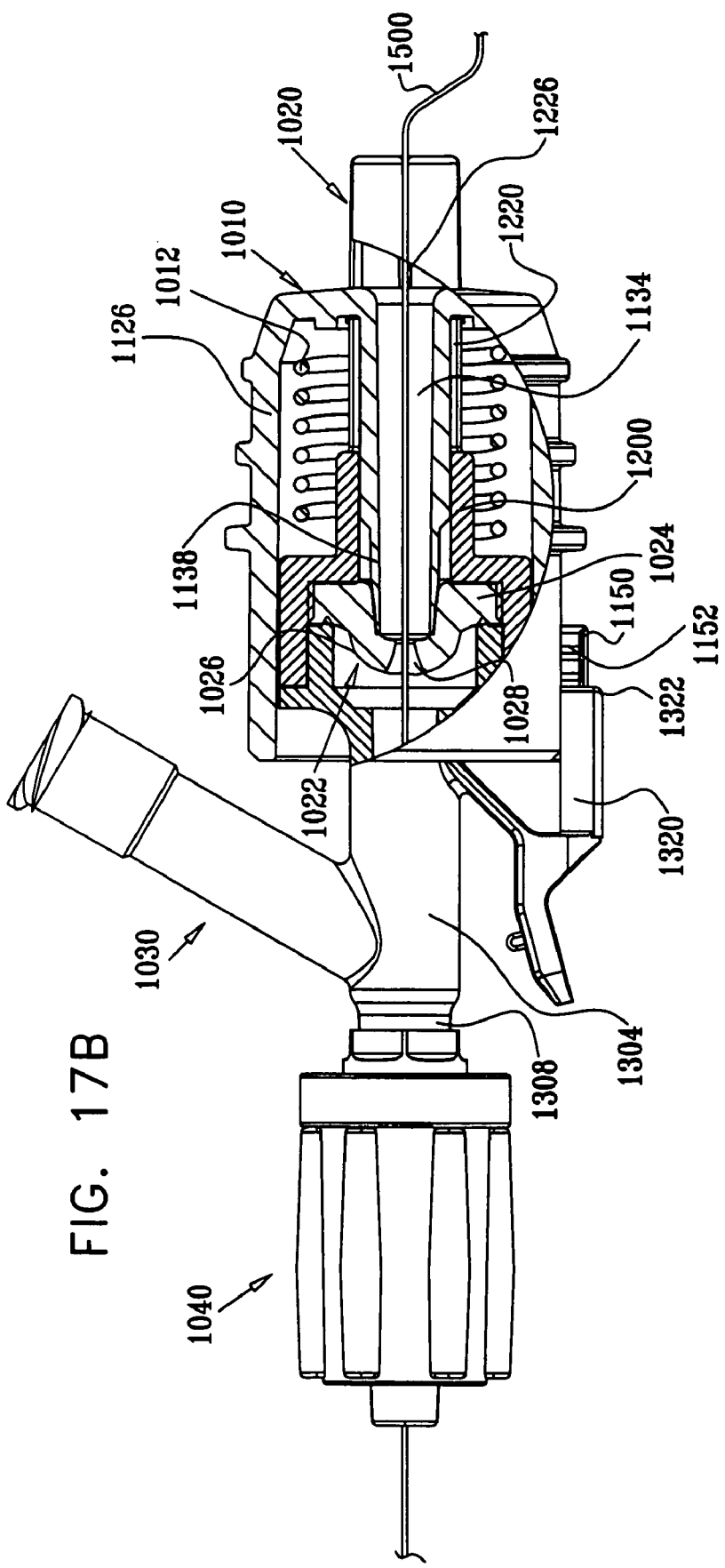
Figure 17C:
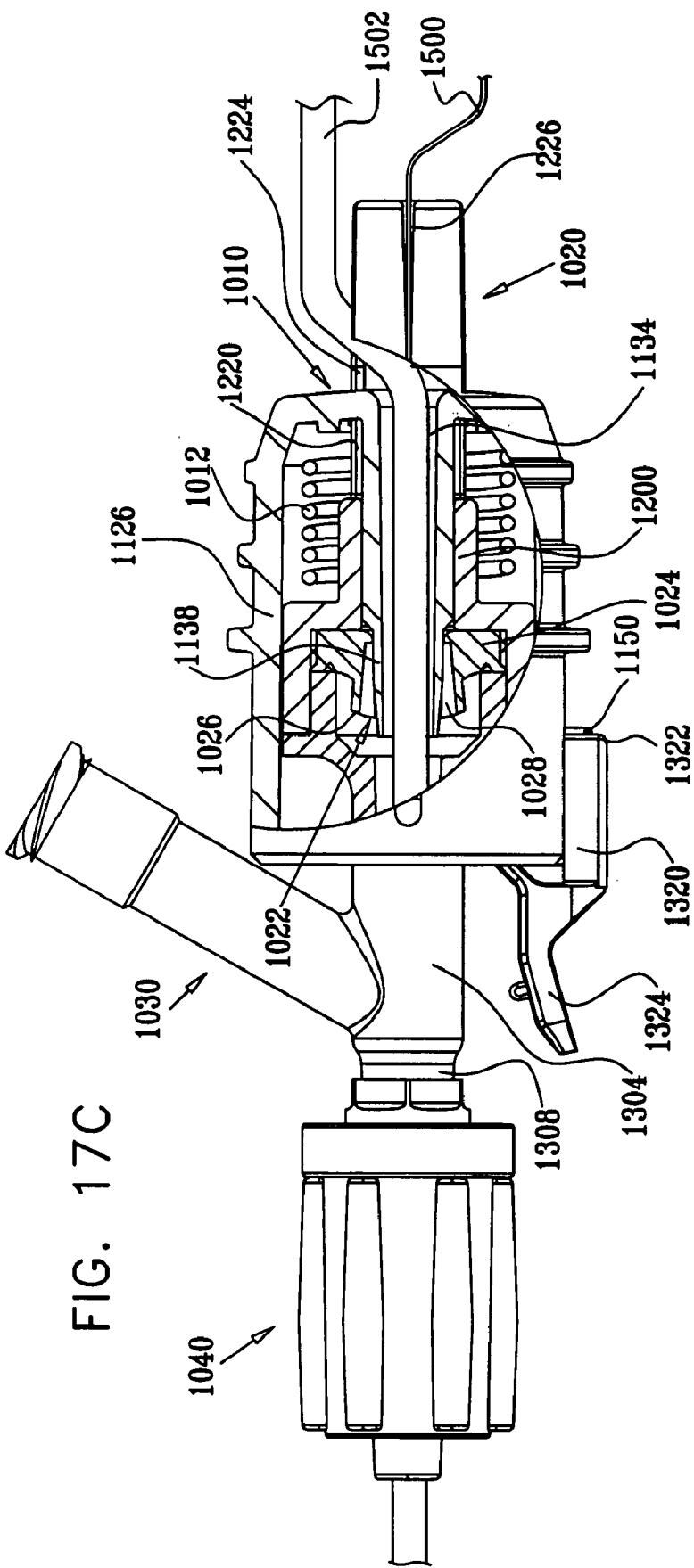
Figure 19A:
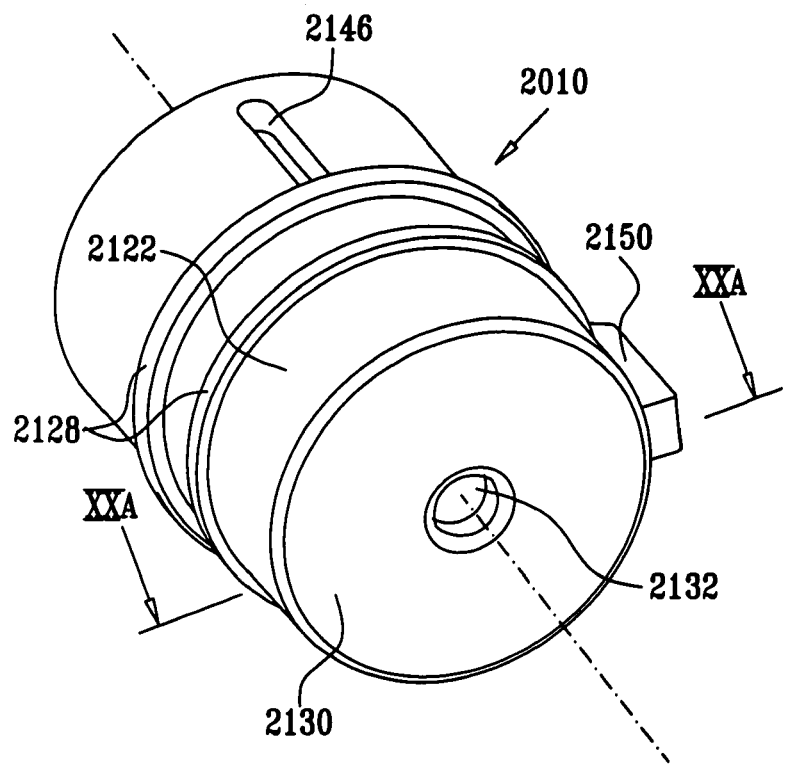
FIGS. 19A and 19B are simplified respective rearward facing and forward facing pictorial illustrations of a rear housing element which forms part of the catheter connection device of FIG. 18.
Figure 19B:
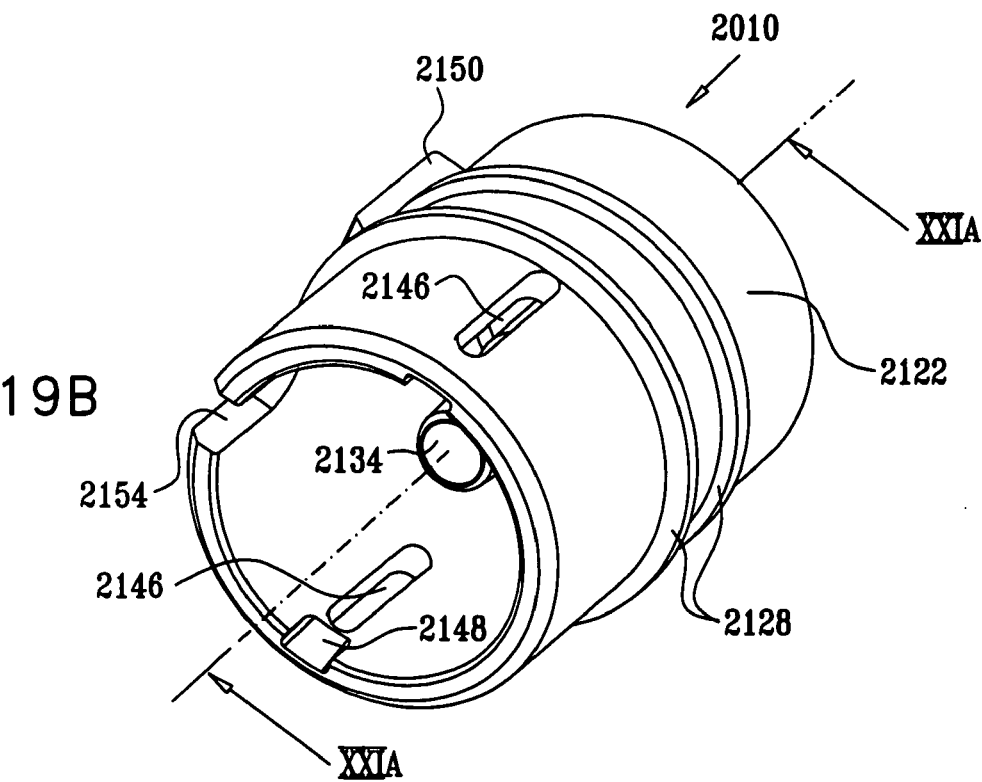
Figure 20A:
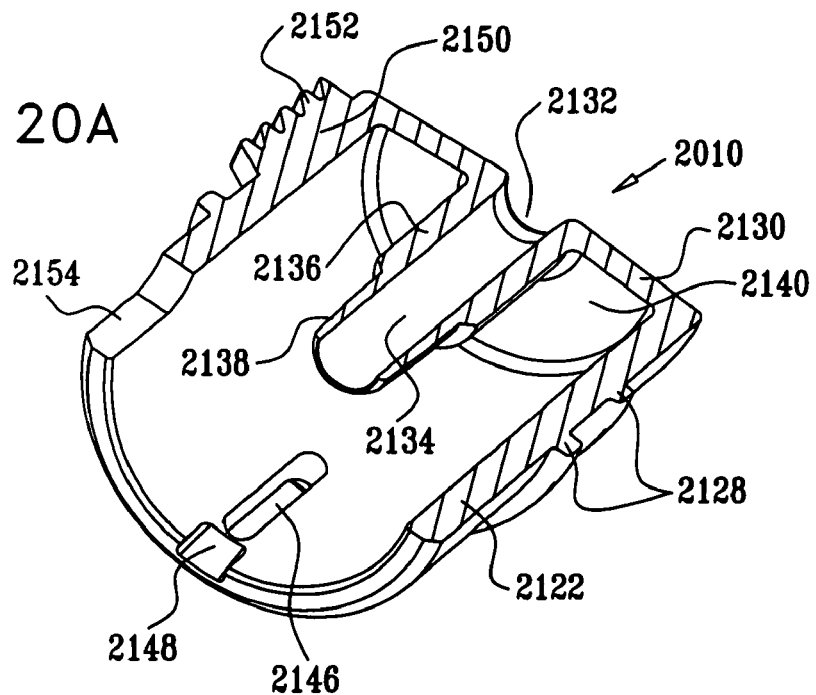
FIGS. 20A and 20B are, respectively, a simplified pictorial sectional illustration and a simplified sectional illustration taken along section lines XXA-XXA in FIG. 19A.
Figure 20B:
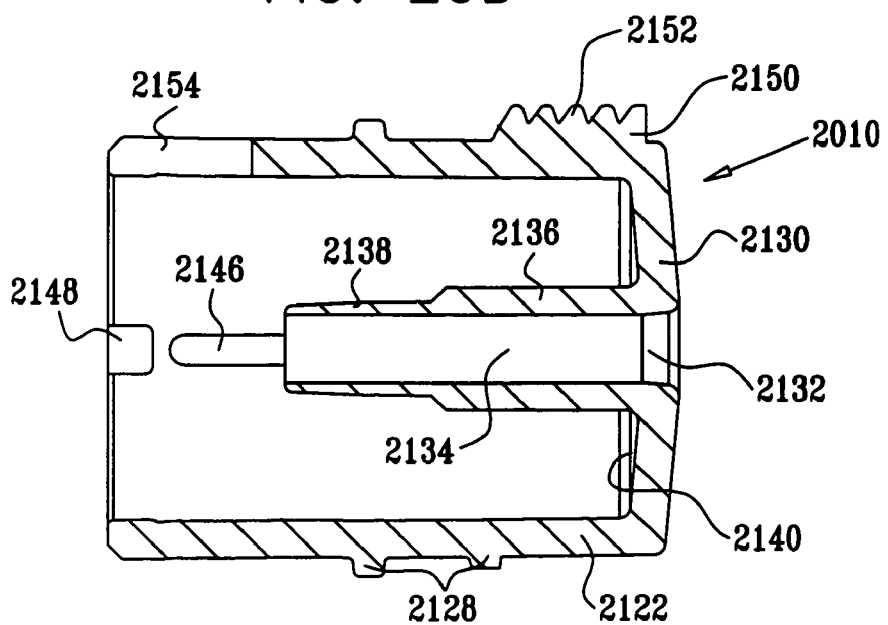
Figure 21A:
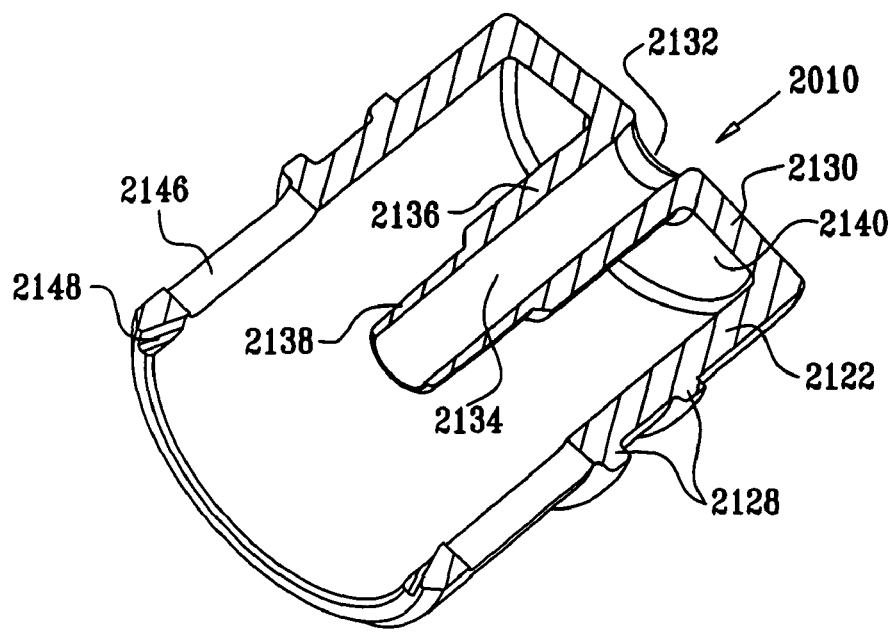
FIGS. 21A and 21B are, respectively, a simplified pictorial sectional illustration and a simplified sectional illustration taken along section lines XXIA-XXIA in FIG. 19B.
Figure 21B:
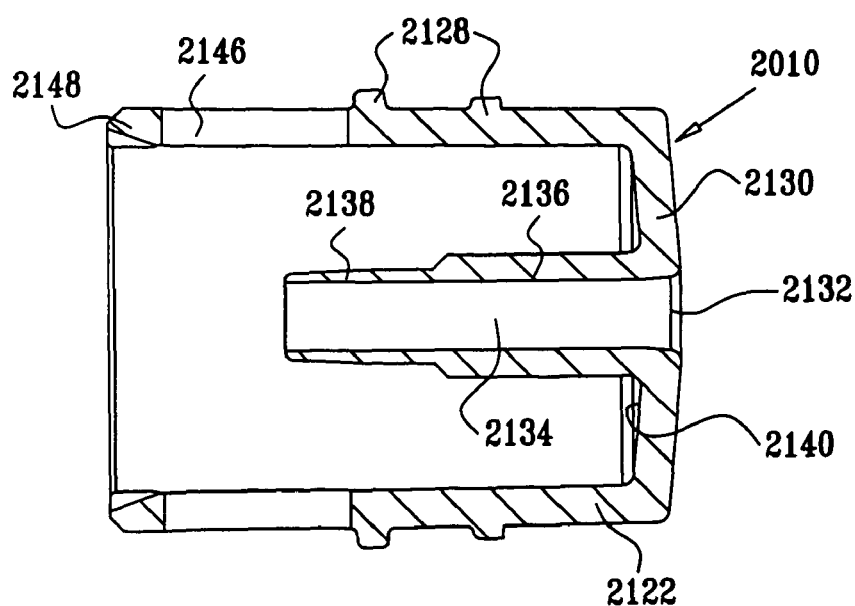
Figure 22A:
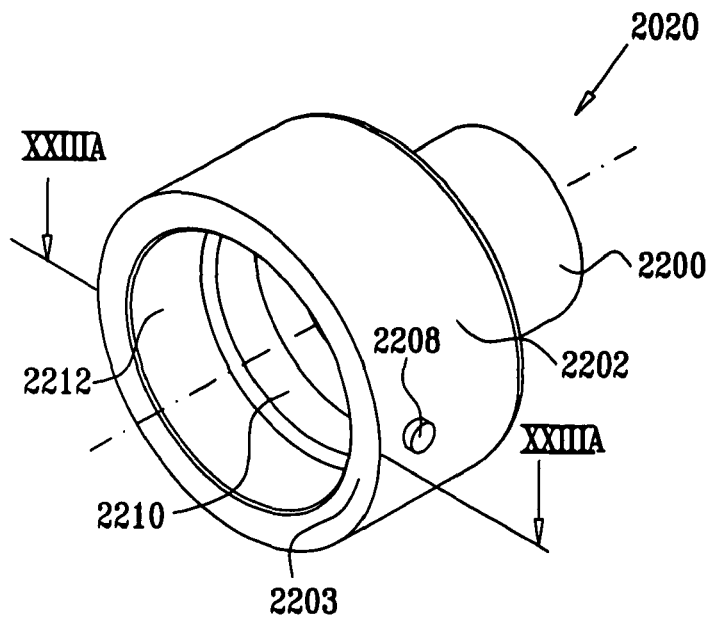
FIGS. 22A and 22B are simplified pictorial illustrations of an intermediate element which forms part of the catheter connection device of FIG. 18.
Figure 22B:
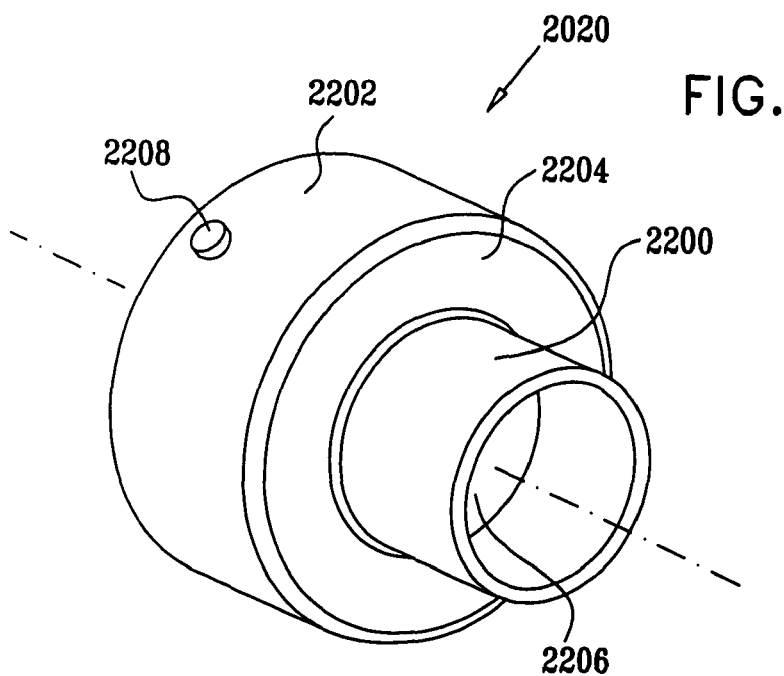
Figure 23A:
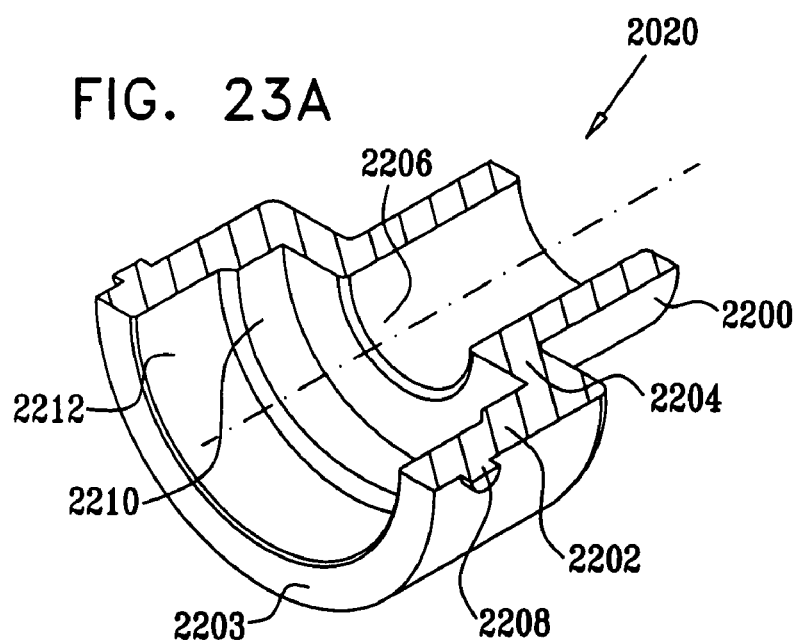
FIGS. 23A and 23B are, respectively, a simplified pictorial sectional illustration and a simplified sectional illustration taken along section lines XXIIIA-XXIIIA in FIG. 22A.
Figure 23B:
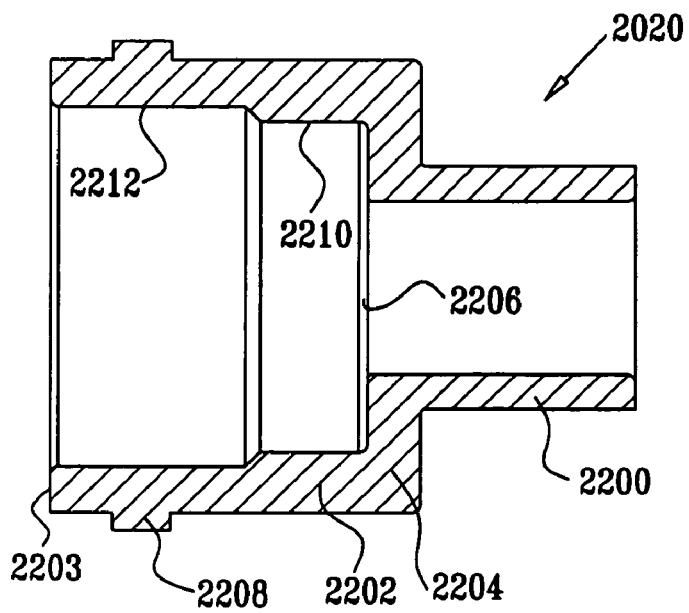
Figure 24A:
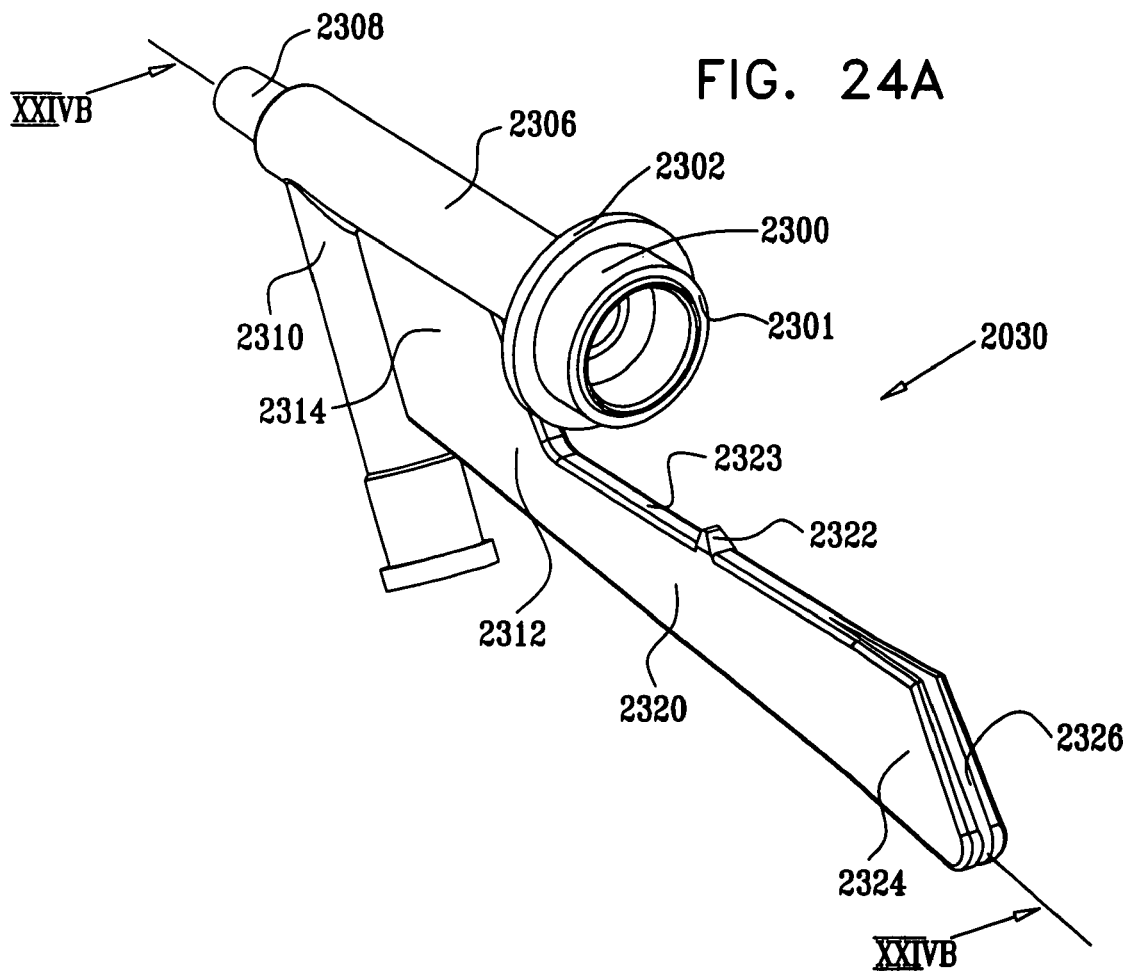
FIGS. 24A and 24B are, respectively, a simplified pictorial illustration and a simplified sectional illustration of a branched connector which forms part of the catheter connection device of FIG. 18, the sectional illustration being taken along section lines XXIVB-XXIVB in FIG. 24A.
Figure 24B:
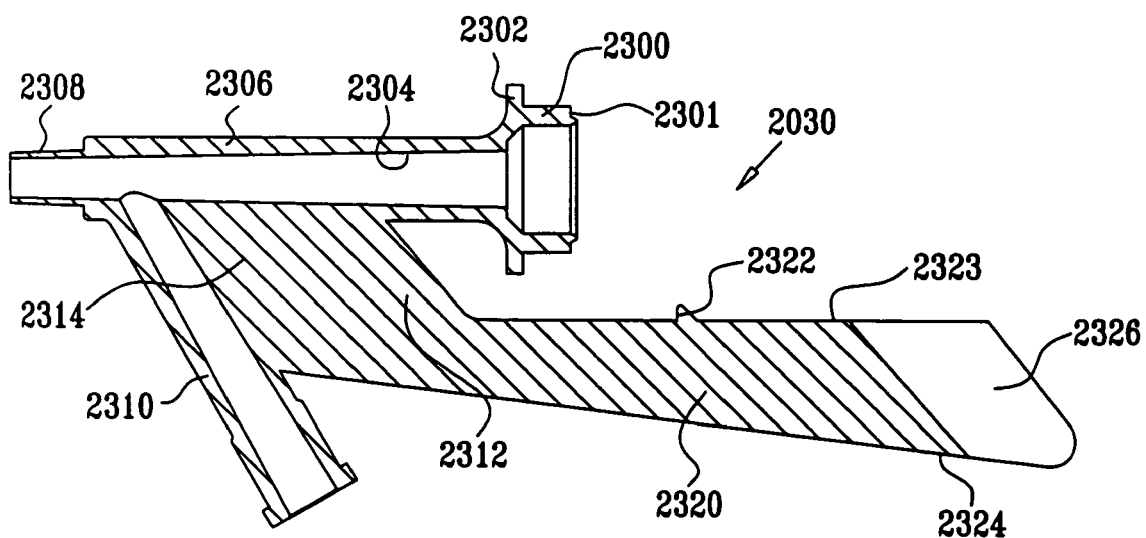
Figure 25A:
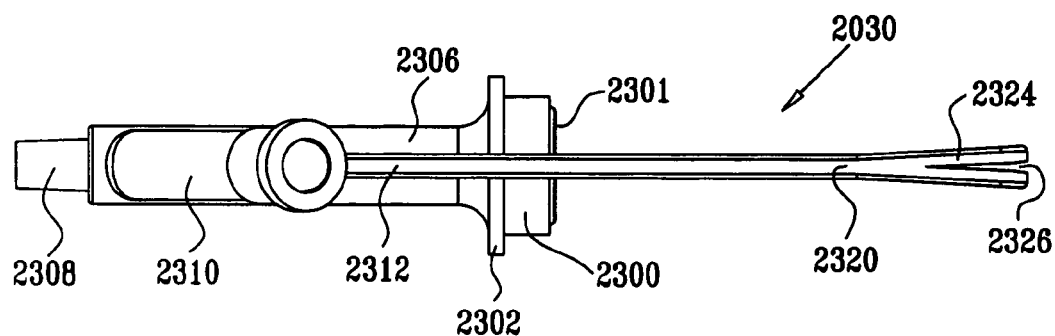
FIGS. 25A and 25B are simplified respective top view and side view planar illustrations of the branched connector of FIGS. 24A and 24B.
Figure 25B:
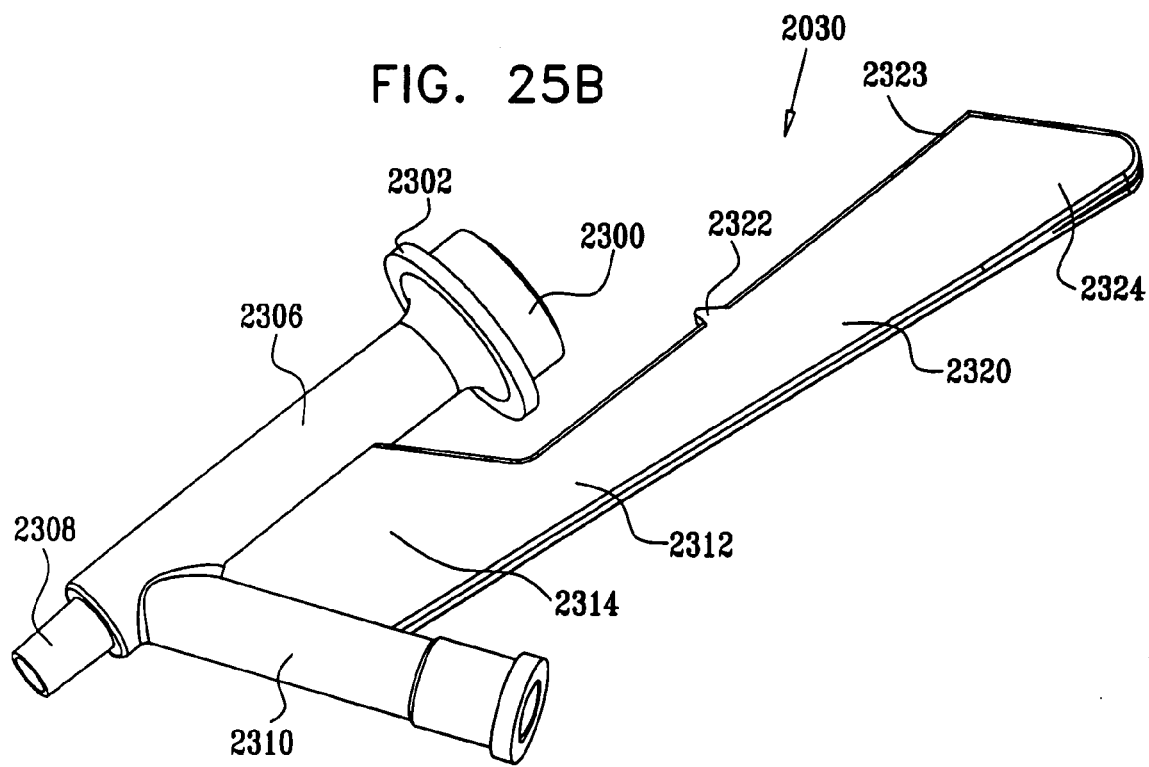

Reference is now made to FIGS. 17A, 17B and 17C which are simplified sectional illustrations of the catheter connection device of FIG. 10 in various operative orientations.

Turning to FIG. 17A, the catheter connection device is shown in a closed operative orientation which is suitable for storage. In this orientation, cylindrical conduit 1134 of rear housing element 1010 is disposed within rearward facing portion 1200 and concave wall portions 1220 of intermediate element 1020, and forward facing portion 1202 of intermediate element 1020 is disposed within cylindrical portion 1126 of forward facing portion 1122 of rear housing element 1010. Protrusions 1208 formed on forward facing cylindrical portion 1202 (not shown) slidingly engage elongate slots 1146 formed in cylindrical section 1126 of rear housing element 1010 (not shown). Spring 1012 is preferably disposed about concave wall portions 1220 and rearward facing portion 1200 of intermediate element 1020. As described hereinabove, concave wall portions 1220 engage the concave slots 1133 of the rear housing element 1010.

Elastomeric element 1022 is seated within forward portion 1202 of intermediate element, 1020, against bulkhead 1204. In this operative orientation slit 1028 is closed.

Rear portion 1300 of branched connector 1030 is seated in forward portion 1202 of intermediate element 1020, such that surface 1203 thereof engages a rearward facing surface of flange 1302 of branched connector 1030, thus maintaining intermediate element 1020 in place. Rearward facing surface 1301 of rear portion 1300 of branched connector 1030 preferably engages disk portion 1024 of elastomeric element 1022, thus maintaining the elastomeric element in place.

Conical portion 1308 of conduit 1304 of branched connector 1030 is disposed within a cylindrical portion of tube connector assembly 1040.

Turning now to FIG. 17B, the catheter connection device is shown in a partially open operative orientation which is suitable for insertion of a narrow tube or guide wire 1500 therethrough. In this orientation, branched connector 1030 is rearwardly displaced, such that tooth 1322 formed on ratchet arm 1320 slides along serrated surface 1152 of ridge 1150 of rear housing element 1010, stopping at a generally central part thereof.

Forward displacement of rear housing element 1010 relative to branched connector 1030 causes relative rearward displacement of intermediate element 1020 within rear housing element 1010, which is accompanied by relative rearward displacement of protrusions 1208 within elongate slots 1146 (not shown). The relative rearward displacement of intermediate element 1020 causes spring 1012 to be partially-axially compressed.

Elastomeric element 1022, which is seated between branched connector 1030 and intermediate element 1020, is relatively rearwardly displaced together with branched connector 1030. Relative rearward displacement of elastomeric element 1022 causes forward facing tapering portion 1138 of cylindrical conduit 1134 to partially extend through cross-shaped slit 1028 of protrusion 1026, thus creating a narrow passage between the rear end of the catheter connector device and the forward end thereof.

As seen in FIG. 17B, the narrow tube 1500 may be inserted from the rear end of the catheter connector device to the forward end thereof via cylindrical conduit 1134, slit 1028, cylindrical conduit 1304, and tube connector assembly 1040. As shown clearly in FIG. 17B, once the narrow tube 1500 is inserted through the catheter connector device, it may be engaged and retained in one of notches 1226, thus preventing axial movement of the tube 1500 relative to rear housing element 1010 and branched connector 1030. Additionally, since the slit 1028 is not fully opened, blood leakage is at least partially prevented.

Turning now to FIG. 17C, the catheter connection device is shown in an open operative orientation which is suitable for insertion of a tube or a balloon catheter therethrough. In this orientation, branched connector 1030 is further rearwardly displaced, such that tooth 1322 formed on ratchet arm 1320 slides along serrated surface 1152 of ridge 1150 of rear housing element 1010, engaging the rearward portion thereof.

Relative rearward displacement of branched connector 1030 causes rearward displacement of intermediate element 1020 within rear housing element 1010, which is accompanied by rearward displacement of protrusions 1208 within elongate slots 1146. The rearward displacement is limited by the engagement of protrusions 1208 with the rearward facing surfaces of slots 1146 (Not shown). The rearward displacement of intermediate element 1020 causes spring 1012 to further compress.

Elastomeric element 1022, which is seated between branched connector 1030 and intermediate element 1020, is rearwardly displaced together with branched connector 1030. Rearward displacement of elastomeric element 1022 causes forward facing tapering portion 1138 of cylindrical conduit 1134 to fully extend through slit 1028 of protrusion 1026, thus creating a wide passageway through the catheter connector device.

As seen in FIG. 17C, a plurality of tubes 1500 and 1502 may be inserted from the rear end of the catheter connector device to the forward end thereof via cylindrical conduit 1134, slit 1028, cylindrical conduit 1304, and tube connector assembly 1040. As shown clearly in FIG. 17C, once the tubes 1500 and 1502 are inserted through the catheter connector device, at least one tube may be engaged and retained in one of notches 1226, thus preventing axial movement of the tube relative to rear housing element 1010 and branched connector 1030. Alternatively or additionally, at least one tube may be held in slots 1224, such that axial movement is enabled. The 90 degree separation of notches 1226 and slots 1224, retains the tubes inserted through the catheter connector device in separate locations such that they do not get tangled.

It is appreciated that the catheter connector device may be manually returned to the closed orientation of FIG. 17A by a user pressing finger engagement extension 1324 of ratchet engagement arm 1320, thus releasing tooth 1322 from serrated surface 1152 of ridge 1150. When the engagement between branched connector 1030 and rear housing element 1010 is released, spring 1012 is released and returns to its fully extended rest position, thus forwardly displacing intermediate element 1020, elastomeric element 1022 and branched connector 1030. It is appreciated that pressing the finger engagement extension 1324 of the ratchet engagement arm 1320 fully releases tooth 1322, such that the tooth cannot get caught again in a manner that the catheter connector device is in a partially closed orientation.

It is appreciated that at the end of the catheterization and following removal of tubing and/or wires, forward displacement of the branched connector 1030 releases the elastomeric element 1022 thus allowing the elastomeric element 1022 to return to its closed position by virtue of its elastomeric properties.

Reference is now made to FIGS. 18-26C, which illustrate a catheter connection device constructed and operative in accordance with yet another preferred embodiment of the present invention. Turning to FIG. 18, it is seen that the catheter connection device comprises a rear housing element 2010, inside of which is located a spring 2012, such as a coil spring, an intermediate element 2020 and an elastomeric element 2022 in the shape of a disc portion 2024 and a forward facing cross-shaped protrusion 2026 integrally formed therewith and centered thereon. Cross-shaped protrusion 2026 is formed with a throughgoing slit 2028 and disk portion 2024 is formed with a partial slit, positioned at a 90 degree angle with respect to slit 2028. Mounted on intermediate element 2020 is a branched connector 2030 onto a forward end of which is mounted a tube connector assembly 2040, such as catalog number 590205 which is commercially available from ELCAM MEDICAL AGRICULTURAL COOPERATIVE ASSOCIATION LTD of Kibbutz Baram, Israel.

Reference is now made to FIGS. 19A-21B, which illustrate the rear housing element 2010. As seen in FIGS. 19A-21B, the rear housing element 2010 comprises a generally cylindrical main portion 2122 having formed thereon a plurality of mutually spaced, generally parallel radially outward facing rings 2128 for improving the grip of the catheter connector device by the user. Alternatively, the rings 2128 may be obviated.

Main portion 2122 terminates at a rearward end thereof in a wall portion 2130, which is formed with a central aperture 2132. A forward facing generally cylindrical conduit 2134, which is centered within main portion 2122, extends forwardly of wall portion 2130 in fluid flow connection with central aperture 2132. Forward facing generally cylindrical conduit 2134 includes a main portion 2136 and a forward facing tapered portion 2138. An inner surface 2140 of wall portion 2130 defines a seat for spring 2012 (FIG. 18).

Formed on main portion 2122 is a pair of elongate slots 2146, which are typically mutually separated by 180 degrees. Disposed forwardly of and aligned with elongate slots 2146 there are preferably formed inwardly and forwardly facing tapered recesses 2148.

Formed on a radially outward surface of forward facing generally cylindrical section 2126 is a ridge 2150 having a serrated surface 2152 on one side wall thereof. Ridge 2150 may be circumferentially separated from elongate slots 2146 by 90 degrees. Disposed forwardly of and aligned with ridge 2150 is preferably formed an elongate generally rectangular cutout portion 2154.

Reference is now made to FIGS. 22A-23B, which illustrate the intermediate element 2020. As seen in FIGS. 22A-23B, intermediate element 2020 comprises a rearward facing, generally cylindrical portion 2200, which is arranged to be disposed about forward facing generally cylindrical conduit 2134 of the rear housing element 2010 (FIGS. 19A-21B), and about which spring 2012 is disposed (FIG. 18).

Integrally formed with rearward facing portion 2200 is a forward facing cylindrical portion 2202 including a forward facing surface 2203. A bulkhead 2204 is defined between rearward facing portion 2200 and forward facing cylindrical portion 2202 and is formed with a central aperture 2206 which communicates therebetween. Forward facing cylindrical portion 2202 is formed with a pair of radially outwardly extending protrusions 2208. The interior surface of forward facing cylindrical portion 2202 includes a relatively narrower rear portion 2210 in which elastomeric element 2022 is seated, and communicating with a relatively wider forward portion 2212.

Reference is now made to FIGS. 24A-25B, which illustrate the branched connector 2030. As seen in FIGS. 24A-25B, the branched connector 2030 comprises a generally cylindrical rear portion 2300 having a rearward facing surface 2301 and a flange 2302. Rear portion 2300 is arranged to be seated within forward portion 2212 of intermediate element 2020 (FIGS. 22A-23B). Communicating with the interior of rear portion 2300 is a generally cylindrical conduit 2304, having a main portion 2306 and a forward facing conical portion 2308. Communicating with main portion 2306 is a branch conduit 2310.

Integrally formed with an outer surface of the branched connector 2030 is an arm portion 2312, including a wide connection surface 2314 connecting the arm portion 2312 with main portion 2306 and branch conduit 2310. Arm portion 2312 additionally includes a generally axially extending substantially flat arm 2320 having a sideways facing outwardly extending tooth 2322 formed on an inwardly facing surface 2323 of arm 2320, for selectable engagement with serrated surface 2152 of ridge 2150 formed on rear housing element 2010 (FIGS. 19A-21B). An outward-facing end 2324 of arm 2320 preferably has a notch 2326 extending therethrough.

Figure 26A:
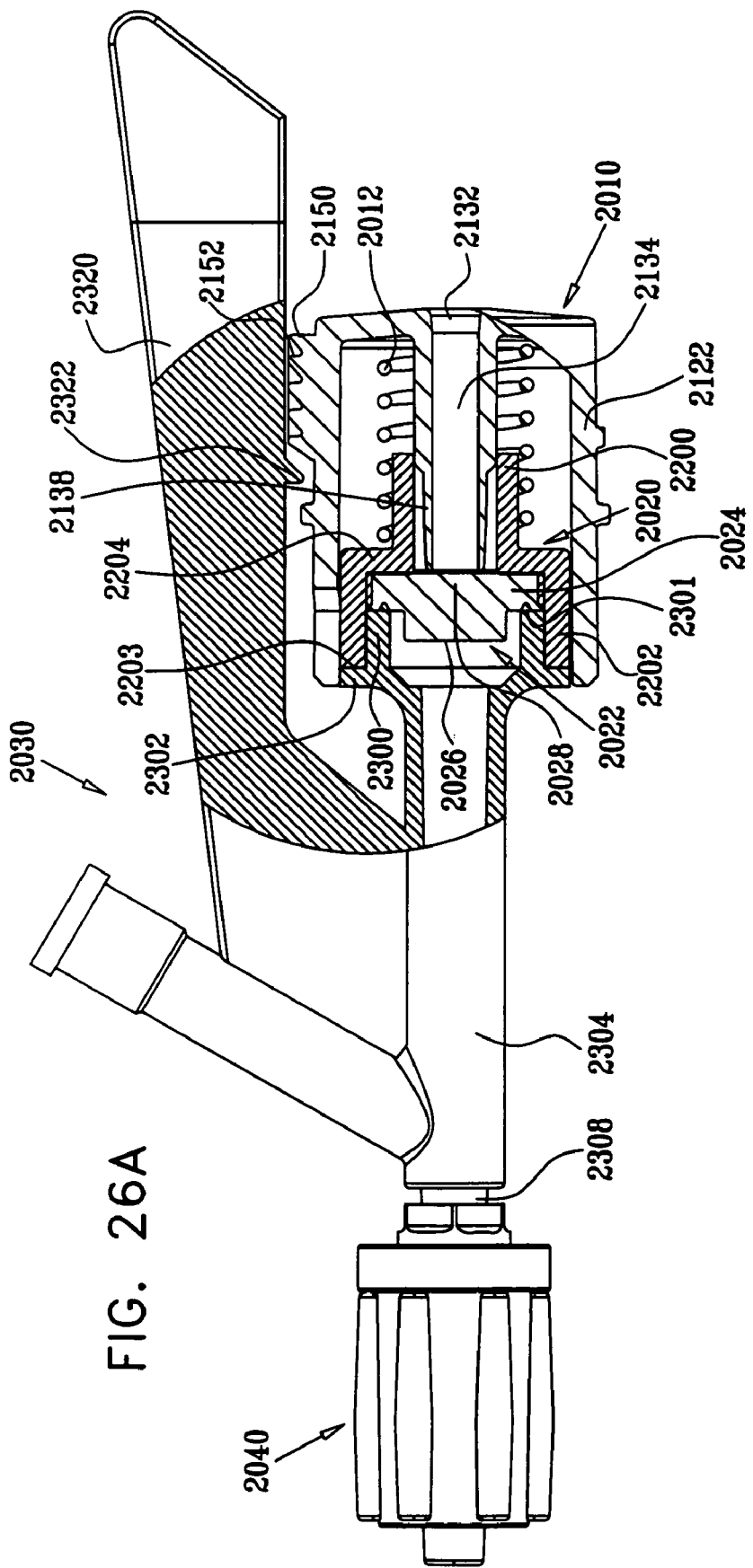
FIGS. 26A, 26B and 26C are partially cutout partially pictorial illustrations of the preferred embodiment of the catheter connection device of FIG. 18 in various operative orientations.
Figure 26B:
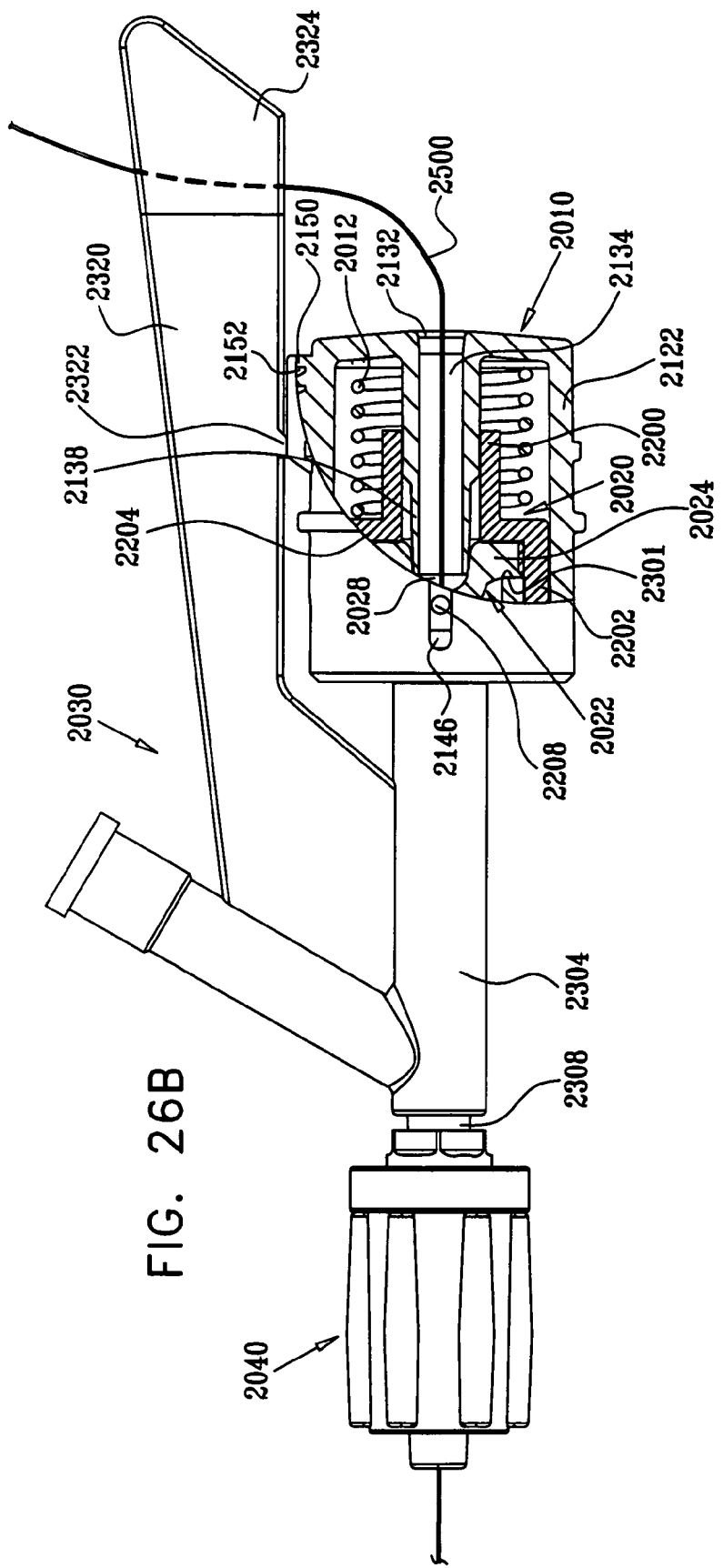
Figure 26C:
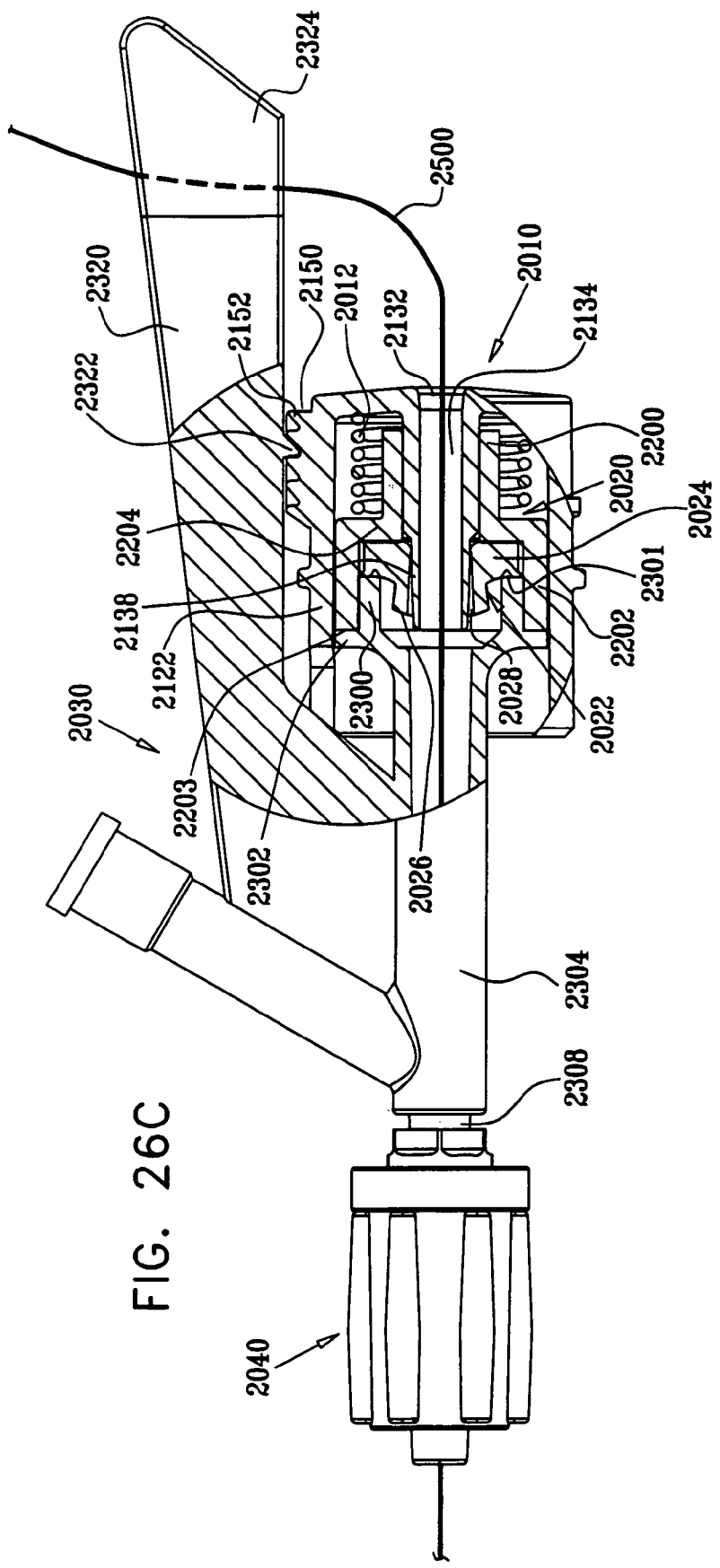

Reference is now made to FIGS. 26A, 26B and 26C which are simplified sectional illustrations of the catheter connection device of FIG. 18 in various operative orientations.

Turning to FIG. 26A, the catheter connection device is shown in a closed operative orientation which is suitable for storage. In this orientation, cylindrical conduit 2134 of rear housing element 2010 is disposed within rearward facing portion 2200 of intermediate element 2020, and forward facing portion 2202 of intermediate element 2020 is disposed within main portion 2122 of rear housing element 2010. Protrusions 2208 formed on forward facing cylindrical portion 2202 slidingly engage elongate slots 2146 formed in main portion 2122 of rear housing element 2010 (not shown). Spring 2012 is preferable disposed about cylindrical conduit 2134 of rear housing element 2010 and rearward facing portion 2200 of intermediate element 2020.

Elastomeric element 2022 is seated within forward portion 2202 of intermediate element 2020, against bulkhead 2204. In this operative orientation cross-shaped slit 2028 formed in protrusion 2026 is closed, and thus a user can pass catheterization tools through the slit without opening it, resulting in reduced bleeding.

Rear portion 2300 of branched connector 2030 is seated in forward portion 2202 of intermediate element 2020, such that surface 2203 thereof engages a rearward facing surface of flange 2302 of branched connector 2030, thus maintaining intermediate element 2020 in place. Rearward facing surface 2301 of rear portion 2300 of branched connector 2030 preferably engages disk portion 2024 of elastomeric element 2022, thus maintaining the elastomeric element in place.

Conical portion 2308 of conduit 2304 of branched connector 2030 is disposed within a cylindrical portion of tube connector assembly 2040.

Turning now to FIG. 26B, the catheter connection device is shown in a partially open operative orientation which is suitable for insertion of a narrow tube or guide wire therethrough. In this orientation, branched connector 2030 is rearwardly displaced, such that tooth 2322 formed on arm 2320 slides along serrated surface 2152 of ridge 2150 of rear housing element 2010, stopping at a generally central part thereof.

Forward displacement of rear housing element 2010 relative to branched connector 2030 causes relative rearward displacement of intermediate element 2020 within rear housing element 2010, which is accompanied by relative rearward displacement of protrusions 2208 within elongate slots 2146 (not shown). The relative rearward displacement of intermediate element 2020 causes spring 2012 to be partially-axially compressed.

Elastomeric element 2022, which is seated between branched connector 2030 and intermediate element 2020, is relatively rearwardly displaced together with branched connector 2030. Relative rearward displacement of elastomeric element 2022 causes forward facing tapering portion 2138 of cylindrical conduit 2134 to partially extend through cross-shaped slit 2028 of protrusion 2026, thus creating a narrow passage between the rear end of the catheter connector device and the forward end thereof.

As seen in FIG. 26B, the narrow tube 2500 may be inserted from the rear end of the catheter connector device to the forward end thereof via cylindrical conduit 2134, slit 2028, cylindrical conduit 2304, and tube connector assembly 2040. As shown clearly in FIG. 26B, once the narrow tube 2500 is inserted through the catheter connector device, it may be engaged and retained in notch 1326, thus preventing axial movement of the tube relative to rear housing element 2010 and branched connector 2030.

Turning now to FIG. 26C, the catheter connection device is shown in an open operative orientation which is suitable for insertion of a tube or a balloon catheter therethrough. In this orientation, branched connector 2030 is further rearwardly displaced, such that tooth 2322 formed on arm 2320 slides along serrated surface 2152 of ridge 2150 of rear housing element 2010, engaging the rearward portion thereof.

Relative rearward displacement of branched connector 2030 causes relative rearward displacement of intermediate element 2020 within rear housing element 2010, which is accompanied by relative rearward displacement of protrusions 2208 within elongate slots 2146. The relative rearward displacement is limited by the engagement of protrusions 2208 with the rearward facing surfaces of slots 2146 (not shown). The relative rearward displacement of intermediate element 2020 causes spring 2012 to be compressed.

Elastomeric element 2022, which is seated between branched connector 2030 and intermediate element 2020, is rearwardly displaced together with branched connector 2030. Rearward displacement of elastomeric element 2022 causes forward facing tapering portion 2138 of cylindrical conduit 2134 to fully extend through slit 2028 of protrusion 2026, thus creating a wide passageway through the catheter connector device.

As seen in FIG. 26C, at least one tube 2500 may be guided from the rear end the catheter connector device and the forward end thereof via cylindrical conduit 2134, slit 2028, cylindrical conduit 2304, and tube connector assembly 2040. As shown clearly in FIG. 26C, once the tubes are inserted through the catheter connector device, at least one tube may be engaged and retained in notch 2326, thus preventing axial movement of the tube relative to rear housing element 2010 and branched connector 2030. It is appreciated that pressing the finger engagement extension 2324 of the ratchet engagement arm 2320 fully releases tooth 2322 such that the tooth cannot get caught again in a manner that the catheter connector device is in a partially closed orientation.

It is appreciated that at the end of the catheterization and following removal of tubing and/or wires, forward displacement of the branched connector 2030 releases the elastomeric element 2022 thus allowing the elastomeric element 2022 to return to its closed position by virtue of its elastomeric properties.

It will be appreciated by persons skilled in the art that the present invention is not limited to what has been particularly shown and described hereinabove. Rather the scope of the present invention includes both combinations and subcombinations of the various features described hereinabove as well as modifications and variations thereof as would occur to a person of skill in the art upon reading the foregoing specification and which are not in the prior art.

The invention claimed is:

1. A connector for coupling to a guiding catheter and comprising:
   a housing defining a conduit which is adapted to communicate with the interior of a guiding catheter when said connector is coupled to said guiding catheter, said housing including first and second housing portions which are manually axially displaceable relative to one another thereby to position said first and second housing portions in various relative mutual axial orientations;
   a selectably openable normally closed valve associated with said conduit for selectable sealing thereof, said selectably openable valve having an open state, a closed state and at least one partially open state realized by suitable relative axial displacement of said first and second housing portions resulting in suitable relative mutual axial orientation thereof and permitting at least one elongate element to extend therethrough, even when said valve is in said closed state, said selectably openable valve including a spring which urges said valve towards said closed state; and
   an automatically engageable and manually disengageable valve state governing mechanism operative for automatically retaining said valve in said open state and in said at least one partially open state against the urging of said spring.

2. A connector for coupling to a guiding catheter according to claim 1 wherein said valve comprises an elastomeric element having at least one slit therethrough.

3. A connector for coupling to a guiding catheter according to claim 1 wherein said automatically engageable and manually disengageable valve state governing mechanism is operative for fully closing said valve in a single stage operation of a user.

4. A connector for coupling to a guiding catheter according to claim 1 wherein said automatically engageable and manually disengageable valve state governing mechanism comprises an engagement arm formed on said second housing element and having formed thereon a tooth and a serrated surface associated with said first housing element for engagement with said tooth.

5. A connector for coupling to a guiding catheter according to claim 4 and wherein depressing of said engagement arm releases said tooth from said serrated surface, thereby releasing the engagement between said first and second housing portions and automatically causing said valve to return to said closed state under the urging of said spring.

6. A connector for coupling to a guiding catheter according to claim 4 and wherein following said relative axial displacement of said first and second housing portions said tooth engages said serrated surface, thereby preventing relative motion between said first and second housing portions and preventing said valve from returning to said closed state under the urging of said spring.

7. A connector for coupling to a guiding catheter according to claim 4 and wherein in said partially open state, said tooth stops at a central portion of said serrated surface and said relative axial displacement of said first and second housing portions creates of a narrow passage in said valve.

8. A connector for coupling to a guiding catheter according to claim 4 and wherein depressing said engagement arm releases said tooth such that said tooth moves automatically to beyond said serrated surface to position said valve in said closed state and cannot engage said serrated surface in said partially open state without first returning to said closed state.

9. A connector for coupling to a guiding catheter and comprising:

a housing defining a conduit, which is adapted to communicate with the interior of a guiding catheter when said connector is coupled to said guiding catheter, said housing including first and second housing portions which are manually axially displaceable relative to one another thereby to position said first and second housing portions in various relative mutual axial orientations, at least one of said first and second housing portions having integrally formed therewith at least one notch; and a selectably openable normally closed valve associated with said conduit for selectable sealing thereof, said selectably openable valve having an open state, a closed state and at least one partially open state realized by suitable relative axial displacement of said first and second housing portions resulting in suitable relative mutual axial orientation thereof and permitting at least one elongate element to extend therethrough, even when said valve is in said closed state, wherein said notch is adapted to have said at least one elongate element inserted thereinto by a user and retained therein, thereby to prevent axial movement of said at least one elongate element relative to at least one of said first and second housing portions when said valve is in any of said open state, said closed state and said at least one partially open state.

10. A connector for coupling to a guiding catheter according to claim 9 wherein said valve comprises an elastomeric element having at least one slit therethrough.

11. A connector for coupling to a guiding catheter according to claim 9 and wherein said housing also comprises at least one slot which is rotationally offset from said at least one notch and which is adapted to have said at least one elongate element inserted thereinto by a user and retained therein such that axial movement of said at least one elongate element relative to at least one of said first and second housing portions is enabled.

12. A connector for coupling to a guiding catheter according to claim 11 wherein said at least one elongate element comprises at least first and second elongate elements, such that said first elongate element is retained in said at least one notch and is maintained separated from said second elongate element which is retained in said at least one slot.

13. A connector for coupling to a guiding catheter according to claim 9 and wherein said notch is formed on a surface of at least one of said first and second housing portions.

* * * * *